United States Patent
Spaulding et al.

(10) Patent No.: US 8,945,521 B2
(45) Date of Patent: Feb. 3, 2015

(54) ENHANCED PHOTOACTIVITY OF SEMICONDUCTORS AND/OR SUNSCREENS

(75) Inventors: Laura A. Spaulding, Wayne, NJ (US); Patricia L. Scott, Union, NJ (US); Alissa R. Frontauria, Lodi, NJ (US)

(73) Assignee: Eveready Battery Company, Inc, St. Louis, MO (US)

( * ) Notice: Subject to any disclaimer, the term of this patent is extended or adjusted under 35 U.S.C. 154(b) by 0 days.

(21) Appl. No.: 13/452,406

(22) Filed: Apr. 20, 2012

(65) Prior Publication Data

US 2012/0269744 A1  Oct. 25, 2012

Related U.S. Application Data

(60) Provisional application No. 61/477,944, filed on Apr. 21, 2011.

(51) Int. Cl.
| | |
|---|---|
| *A61K 8/90* | (2006.01) |
| *A61K 8/40* | (2006.01) |
| *A61K 8/81* | (2006.01) |
| *A61K 8/27* | (2006.01) |
| *A61K 8/29* | (2006.01) |
| *A61Q 17/04* | (2006.01) |

(52) U.S. Cl.
CPC ... *A61K 8/90* (2013.01); *A61K 8/27* (2013.01); *A61K 8/29* (2013.01); *A61K 8/40* (2013.01); *A61Q 17/04* (2013.01); *A61K 8/8117* (2013.01)
USPC ................. 424/59; 424/60; 252/588; 252/589

(58) Field of Classification Search
USPC ..................................... 424/59, 60
See application file for complete search history.

(56) References Cited

U.S. PATENT DOCUMENTS

| | | |
|---|---|---|
| 5,587,148 A | 12/1996 | Mitchell et al. |
| 5,618,522 A | 4/1997 | Kaleta |
| 5,776,440 A | 7/1998 | Forestier |
| 5,939,053 A | 8/1999 | Forestier |
| 6,060,041 A | 5/2000 | Candau |
| 6,165,450 A | 12/2000 | Chaudhuri et al. |
| 6,235,271 B1 | 5/2001 | Luther |
| 6,294,158 B1 | 9/2001 | Dupuis |
| 6,361,782 B1 | 3/2002 | Chevalier et al. |
| 6,440,402 B1 | 8/2002 | Gonzalez |
| 6,444,647 B1 | 9/2002 | Robinson |
| 6,492,326 B1 | 12/2002 | Robinson |

(Continued)

OTHER PUBLICATIONS

Cosmosurf CE Series, Datasheet [online], Surfa Tech Corporation, 2009 [Retrieved on Oct. 31, 2012]. Retrieved from the Internet; <URL: http://www.surfatech.com/pdfs/COSMOSURF_CE_SERIES.pdf (SurfaTech; p. 2, Standard Products, Applications.*

(Continued)

*Primary Examiner* — Jane C Oswecki
(74) *Attorney, Agent, or Firm* — Energizer Personal Care, LL

(57) ABSTRACT

A composition comprising a physical sunscreen, one or more adjuvants, and a carrier oil is provided. The composition also includes at least one of a compound having multiple phenyl groups, a film former or dispersant, and a silicone surfactant. The composition may also include an organic sunscreen. The combination of these ingredients exhibits an unexpected synergistic effect, in that the photoactive properties of the composition (e.g., SPF, UV absorption) are significantly higher than would be predicted based on the values for each of the components individually.

15 Claims, 12 Drawing Sheets

(56) References Cited

U.S. PATENT DOCUMENTS

| | | | |
|---|---|---|---|
| 6,500,411 | B2 | 12/2002 | SenGupta |
| 6,716,418 | B2 | 4/2004 | SenGupta |
| 6,881,776 | B2 | 4/2005 | Butuc |
| 7,098,189 | B2 | 8/2006 | Malik |
| 7,108,860 | B2 | 9/2006 | Dueva et al. |
| 7,276,230 | B2 | 10/2007 | Gonzalez |
| 2004/0009130 | A1 | 1/2004 | Detore et al. |
| 2005/0004274 | A1 | 1/2005 | Healy et al. |
| 2005/0013781 | A1 | 1/2005 | Dueva-Koganov |
| 2007/0006802 | A1 | 1/2007 | Nause |
| 2007/0135535 | A1 | 6/2007 | Hwang et al. |
| 2007/0196295 | A1 | 8/2007 | Cantwell et al. |
| 2008/0107615 | A1 | 5/2008 | Keene et al. |
| 2008/0112904 | A1 | 5/2008 | Traynor et al. |
| 2009/0035234 | A1* | 2/2009 | Cunningham et al. .......... 424/59 |
| 2009/0057627 | A1 | 3/2009 | Bonda et al. |
| 2009/0186055 | A1 | 7/2009 | Dumousseaux et al. |
| 2010/0021403 | A1* | 1/2010 | Bonda et al. .................... 424/59 |
| 2010/0119465 | A1* | 5/2010 | Spaulding et al. .............. 424/60 |

OTHER PUBLICATIONS

International Preliminary Report on Patentability dated Mar. 29, 2012 from corresponding International Patent Application No. PCT/US2010/049106, 7 pages.

International Search Report and Written Opinion Dated Aug. 11, 2009 From PCT/US2009/03526.

Definition of Photoconductivity From Wikipedia (http://en.wikipedia.org/wiki/Photoconductivity).

Definition of Semiconductor From Wikipedia (http://en.wikipedia.org/wiki/Semiconductor).

Definition of Bandgap From Wikipedia (http://en.wikipedia.org/wiki/Bandgap).

List of Semiconductor Materials From Wikipedia (http://en/wikipedia.org/wiki/List_of_semiconductor_materials).

International Search Report and Written Opinion Dated Nov. 1, 2010 From PCT/US2010/49106.

Office Action Dated Sep. 9, 2011 From U.S. Appl. No. 12/483,943.

International Preliminary Report on Patentibility Dated Feb. 18, 2011 From PCT/US2009/03526.

International Preliminary Report on Patentibility Dated Mar. 20, 2012 From PCT/US2010/049106.

Cosmosurf CE Series, Datasheet [Online]. Surfa Tech Corporation, 2009 [Retrieved on Oct. 31, 2012]. Retrieved From the Internet: <URL: http://www.surfatech.com/pdfs/COSMOSURF_CE_SERIES.pdf (Surfatech; p. 2, Standard Products, Applications.

International Search Report and Written Opinion Dated Dec. 6, 2012 From Corresponding International Application No. PCT/US12/34522.

* cited by examiner

US 8,945,521 B2

ENHANCED PHOTOACTIVITY OF SEMICONDUCTORS AND/OR SUNSCREENS

CROSS-REFERENCE TO RELATED APPLICATIONS

The present application claims the benefit of U.S. Provisional Patent Application No. 61/477,944, filed on Apr. 21, 2011.

BACKGROUND OF THE DISCLOSURE

1. Field of the Disclosure

The present disclosure relates to enhancing the photoactivity, such as the sun protection factor (SPF), and/or the UVA (ultraviolet-A) and/or UVB (ultraviolet-B) absorption, of semiconductors that behave as physical sunscreens. In particular, the present disclosure relates to enhancing the photoactivity of physical sunscreens by placing the sunscreens in a composition with one or more compounds that exhibit minimal, if any, photoactivity on their own. The physical sunscreens may also be subsequently placed in photoprotective compositions that include additional sunscreens.

2. Description of the Related Art

It is always a goal in the field of suncare to either use less sunscreen active material while maintaining a desired level of SPF and/or UVA absorption, or to achieve a very high SPF or UVA absorption rate overall. Thus, there is a need for a way of enhancing the photoactivity of semiconductor materials, which can boost the SPF, and/or UVA absorption of these materials.

SUMMARY OF THE DISCLOSURE

The present disclosure provides a composition (e.g., a dispersion or emulsion) of one or more physical sunscreens and/or one or more adjuvants. The one or more adjuvants are selected from the group consisting of ethylhexyl methoxycrylene (or derivatives thereof), compounds having multiple phenyl rings, silicone surfactant, a film former/dispersant, carrier oil, and any combinations thereof. The carrier oil may be aromatic or non-aromatic. The compositions of the present disclosure can take the form of oil-in-water emulsion, water-in-oil emulsion, or an oily liquid that is not an emulsion. They can also be in the form of a cream, lotion, liquid or stick composition.

In one exemplary embodiment, the composition comprises a physical sunscreen, ethylhexyl methoxycrylene, a compound having multiple phenyl rings, and an aromatic and/or non-aromatic carrier oil.

In another exemplary embodiment, the composition comprises a physical sunscreen that is complexed with a silicone surfactant, and an aromatic and/or non-aromatic carrier oil. In a further embodiment of this composition, the composition also has a compound having multiple phenyl rings.

In a further exemplary embodiment, the composition comprises a physical sunscreen that is complexed with a silicone surfactant, ethylhexyl methoxycrylene, and an aromatic and/or non-aromatic carrier oil. In further embodiment of this composition, the composition also has a compound having multiple phenyl rings.

In a still further exemplary embodiment, the composition has ethylhexyl methoxycrylene and a film former/dispersant.

In a yet further exemplary embodiment, the composition comprises a physical sunscreen that is either plain or complexed with a silicone surfactant, a film former/dispersant, and an aromatic and/or non-aromatic carrier oil. In a further embodiment of this composition, the composition also has ethylhexyl methoxycrylene, and a compound having multiple phenyl rings.

In another exemplary embodiment, the composition comprises a physical sunscreen that is complexed with a silicone surfactant, ethylhexyl methoxycrylene, a film former/dispersant, and an aromatic and/or non-aromatic carrier oil.

In another exemplary embodiment, the present disclosure provides composition comprising 0.5% w/w to 30% w/w of a physical sunscreen, 0.1% w/w to 6.0% w/w of ethylhexyl methoxycrylene, a carrier oil, and at least one of a compound having multiple phenyl groups, a silicone surfactant, and a dispersant.

In another exemplary embodiment, the present disclosure provides a composition comprising 0.5% w/w to 30% w/w of a physical sunscreen selected from the group consisting of titanium dioxide, zinc oxide, coated zinc oxide, or a combination thereof, 0.1% w/w to 6.0% w/w of ethylhexyl methoxycrylene, 0.2% w/w to 1.0% w/w of a compound having multiple phenyl groups selected from the group consisting of benzene sulfonic acids, salts of benzene sulfonic acids, styrenic block copolymers with a hydrogenated midblock of styrene-ethylene /butylene-styrene, styrenic block copolymers with a hydrogenated midblock of styrene-ethylene/propylene-styrene, styrene/butadiene/styrene block copolymers, styrene/isoprene/styrene block copolymers, ethylene/butadiene/styrene block copolymer, ethylene/propylene/styrene block copolymer, styrene/ethylene/butylene block copolymer, styrene/propylene/butadiene block copolymer, and derivatives or combinations thereof, and a carrier oil.

DETAILED DESCRIPTION OF THE DISCLOSURE

Figure 1:
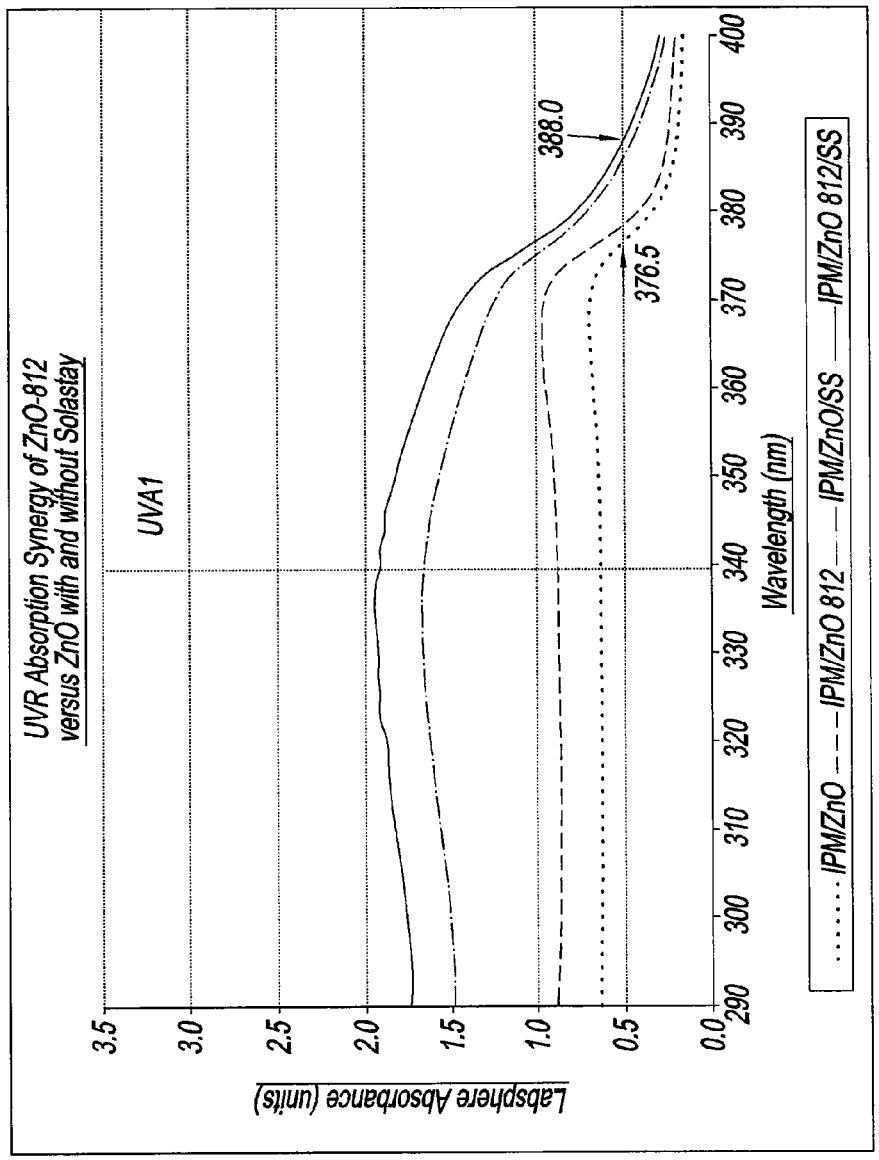
FIGS. 1-12 depict graphs that illustrate the photoactivity of the compositions of the present disclosure, and are discussed in greater detail below.

The present disclosure has unexpectedly discovered that when one or more physical sunscreens and/or one or more adjuvants are combined, the photoactivity of the physical sunscreens and/or adjuvants are greatly enhanced. As is discussed in greater detail below, this result is surprising in that the one or more additional components exhibit very little, if any, photoactivity on their own.

to A "synergistic effect" is defined as the difference in an observed property between a combination of elements, and the sum of the values of that property for each of those elements individually. For example, a synergistic effect on the SPF of a sunscreen composition is observed when the SPF of the composition is greater than the sum of the SPF values for each of the ingredients in the composition.

The physical sunscreen can be any compound that at least partially physically blocks UVR, although it may absorb UVR as well. Suitable physical sunscreens for the compositions of the present disclosure can be one or more semiconductors selected from the group recited in the Wikipedia page, "List of semiconductor materials," found at http://en.wikipedia.org/wiki/List_of_semiconductor_materials, which is herein incorporated by reference. In one embodiment, the physical sunscreen is titanium dioxide, zinc oxide, complexed zinc oxide, or a combination thereof. In a further embodiment, such as those shown below in the experimental data, the sunscreen is zinc oxide.

The physical sunscreen can be present in an amount of from 0.5% w/w to 30% w/w based on the total weight of the composition, or any subranges in between. The zinc oxide can be in the powder form, such as that sold under the trade name Zano® 10, from Umicore. An example of complexed zinc oxide is Zano® 10 Plus, also from Umicore. Titanium dioxide is sold under the trade names Kemira UV Titan, or those available from Kobo. Many other trade names for treated and plain zinc oxide and titanium dioxide exist, as listed in the International Cosmetic Ingredient Dictionary and Handbook.

Ethylhexyl methoxycrylene (EHM), sold under the trade name Solastay® S1 by Hallstar, or derivatives thereof can be present in the composition. EHM can be present in an amount of from 0.1% w/w to 6.0% w/w, based on the total weight of the composition, from 0.2% w/w to 2.0% w/w based on the total weight of the composition, from 0.5% w/w to 2.0% w/w based on the total weight of the composition, or any subranges in between.

The compounds having multiple phenyl compounds can be selected from: benzene sulfonic acids or salts thereof, styrenic block copolymers with a hydrogenated midblock of styrene-ethylene/butylene-styrene (SEBS), styrenic block copolymers with a hydrogenated midblock of styrene-ethylene/propylene-styrene (SEPS), styrene/butadiene/styrene (SBS) block copolymers, styrene/isoprene/styrene (SIS) block copolymers, an ethylene/butadiene/styrene (EBS) block copolymer, an ethylene/propylene/styrene (EPS) block copolymer, styrene/ethylene/butylene (SEB) block copolymer, styrene/propylene/butadiene (SPB) block copolymer, and any derivatives, or any combinations thereof. Examples of the SEBS, SEPS, SBS, SIS, EBS, EPS, SEB, and SPB block copolymers are the Kraton® D and Kraton® G series from Kraton Polymers. In one embodiment, the compound having multiple phenyl groups is the SEB block copolymer, sold under the trade name Kraton® G1650. An example of a benzene sulfonic acid salt is sodium polystyrene benzene sulfonate (available, for example, as Flexan® II, from AzkoNobel).

The compound with multiple phenyl groups can be present in an amount of from 0.1% w/w to 4.0% w/w, based on the total weight of the composition, from 0.2% w/w to 1.0% w/w, based on the total weight of the composition, from 0.25% w/w to 0.5% w/w, based on the total weight of the composition, or any subranges in between.

In one embodiment, the silicone surfactant can be lauryl polyethylene glycol (PEG)-8 dimethicone. Examples include Silube® J208-612 and J208-812, sold by Siltech LLC. The differences between the two types are discussed in greater detail below. The silicone surfactants of the present disclosure may also include variations of the lauryl PEG-8 dimethicone where the PEG group is up to and including PEG-20. In addition, the polypropylene oxide (PPO) and the PEG/PPO variations of the dimethicone may be used. Any of these compounds may be straight chain, have increased alkyl chain length, and/or can be branched, saturated or unsaturated, or aromatic. The silicone surfactant may be present in an amount of from 0.1% w/w to 10.0% w/w based on the total weight of the composition, or any subranges in between.

In one embodiment, the film former/dispersant can be octyldodecyl-propyl-citrate. One commercially available example is Cosmosurf® CE100, available from SurfaTech. The film former/dispersant can be present in an amount of from 0.5% w/w to 20% w/w based on the total weight of the composition, or any subranges in between. Octyldodecyl-propyl-citrate can also exhibit adjuvating activity.

The carrier oil can be one or more oils suitable for the purpose of allowing the phenyl compounds to interact with the semiconductors in the manner discussed below. In one embodiment, the carrier oil can be one or more esters. The esters can be benzoate or non-benzoate esters, with alkyl chain lengths that are branched or non-branched. In another embodiment, the carrier oils used in this disclosure can be those with low polarity that do not exhibit meaningful SPF, such as mineral oil and isopropyl myristate. The carrier oils can also be those with comparatively higher polarity and measurable SPF, such as butyloctyl salicyclate and ethylhexyl salicyclate, the latter of which is also known as octisalate. Examples of commercially available esters suitable for use in the composition of the present disclosure include, but are not limited to, the Finsolv® benzoate esters available from Innospec Active Chemicals, the Schercemol® or Hydramol® esters available from the Lubrizol Corporation, or the Crodamol® esters available from Croda Worldwide. In general, carrier oils can be aromatic and/or non-aromatic esters, and aromatic and/or nonaromatic hydrocarbon liquids. Non-aromatic versions can include straight and/or branched hydrocarbon chains, and saturated and/or unsaturated hydrocarbon chains.

The amount of carrier oil used in the composition will depend on the amounts of the other ingredients. In one embodiment, the amount of carrier oil that will be present in the composition is the remainder after any or all of the ingredients above are incorporated into the composition. The amount of carrier oil may also be such that another carrier may be used, such as water. In one embodiment, the carrier oil is present in an amount of 5-95% w/w, based on the total weight of the emulsion or other type of photoprotective composition, or any subranges in between.

The compositions of the present disclosure can be further used in conjunction with compositions containing organic sunscreens, as the compositions of the present disclosure may enhance the photoactivity of those sunscreens as well as the physical sunscreens discussed above. Suitable organic sunscreens may include, but are not limited to, cinnamates, octisalate, p-aminobenzoic acid, its salts and its derivatives (ethyl, isobutyl, glyceryl esters; p-d imethylaminobenzoic acid); anthranilates (o-aminobenzoates; methyl, menthyl, phenyl, benzyl, phenylethyl, linalyl, terpinyl, and cyclohexenyl esters), salicylates (octyl, amyl, phenyl, benzyl, menthyl (homosalate), glyceryl, and dipropyleneglycol esters), cinnamic acid derivatives (menthyl and benzyl esters, alpha-phenyl cinnamonitrile; butyl cinnamoyl pyruvate), dihydroxycinnamic acid derivatives (umbelliferone, methylumbelliferone, methylaceto-umbelliferone), camphor derivatives (3-benzylidene, 4-methylbenzylidene, polyacrylamidomethyl benzylidene, benzalkonium methosulfate, benzylidene camphor sulfonic acid, and terephthalylidene dicamphor sulfonic acid), trihydroxycinnamic acid derivatives (esculetin, methylesculetin, daphnetin, and the glucosides, esculin and daphnin), hydrocarbons (diphenylbutadiene, stilbene), dibenzalacetone and benzalacetophenone, naptholsulfonates (sodium salts of 2-naphthol-3,6-disulfonic and of 2-naphthol-6,8-disulfonic acids), dihydroxy-naphthoic acid and its salts, o- and p-hydroxydiphenyldisulfonates, coumarin derivatives (7-hydroxy, 7-methyl, 3-phenyl), diazoles (2-acetyl-3-bromoindazole, phenyl benzoxazole, methyl naphthoxazole, various aryl benzothiazoles), quinine salts (bisulfate, sulfate, chloride, oleate, and tannate), quinoline derivatives (8-hydroxyquinoline salts, 2-phenylquinoline), hydroxy- or methoxy-substituted benzophenones, uric and vilouric acids, tannic acid and its derivatives, hydroquinone, benzophenones (oxybenzone, sulisobenzone, dioxybenzone, benzoresorcinol, 2,2',4,4'-tetrahydroxybenzophenone, 2,2'-dihydroxy-4,4'-dimethoxybenzophenone, octabenzone), dibenzoylmethane derivatives, avobenzone, 4-isopropyldibenzoylmethane, butylmethoxydibenzoylmethane, 4-isopropyl-dibenzoylmethane, octocrylene, drometrizole trisiloxane, bemotrizinol (sold under the trade name Tinasorb®), ecamsule (sold under the trade name Mexoryl®), and any combinations thereof.

Data illustrating the benefits of the above-described embodiments of the composition of the present disclosure are shown below. For convenience's sake, the compounds are referred to by their trade names.

Materials Used

ZnO Powder, Zano 10 from Umicore INCI: Zinc oxide Physical Sunscreen Active

Solastay S1 from Hallstar INCI: Ethylhexyl methoxycrylene Sunscreen Photostabilizer Silube J208-612, SILTECH LLC INCI: Lauryl PEG-8 Dimethicone Water-in-oil silicone surfactant

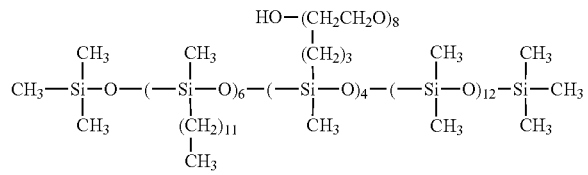

Silube J208-812, SILTECH LLC INCI: Lauryl PEG-8 Dimethicone Water-in-oil Silicone Surfactant

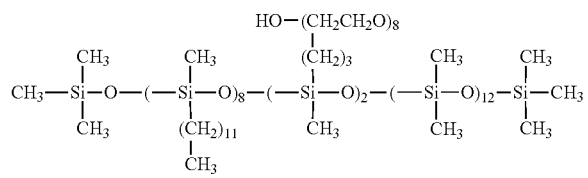

Cosmosurf CE100, SurfaTech INCI: Octyldodecyl-propylcitrate Film Former, Dispersant

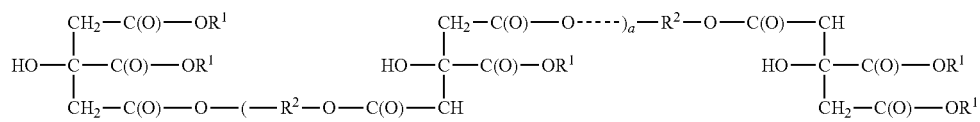

$R^1$ is

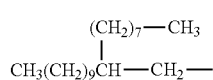

$R^2$ is —$(CH_2)_3$—.

Dispersions Used

K/MO 5% Kraton G1650 (K, Kraton) in Isopropyl Myristate (IPM)

K/IPM 5% Kraton G1650 (K, Kraton) in Isopropyl Myristate (IPM)

K/BHB 5% Kraton G1650 (K, Kraton) in Butyloctyl Salicylate (BHB)

K/OS 5% Kraton G1650 (K, Kraton) in Ethylhexyl Salicylate (OS)

ZnO-GEMS (Gelling Electrostatic Matrix)

ZnO-612: 2% J208-612 electrostatically complexed with 98% ZnO

ZnO-812: 2% J208-812 electrostatically complexed with 98% ZnO

Other ratios of GEM complexed with ZnO are contemplated by the present disclosure.

Instrumentation

The in-vitro SPF was determined using the Labsphere 2000S UV Transmittance Analyzer and PMMA roughened surface substrates. Exceptions and dose amounts are noted at the bottom of the Tables. The Labsphere uses a xenon flashlamp supplying sufficient energy for the spectral range of 250-450 nm.

The in-vivo data was generated using an outside testing facility; FDA monograph; 3 subject panels; static testing only.

Solvent polarity was determined using the Scientifica 870 Liquid Dielectric Constant Meter.

Study 1

In a cursory study to identify active agents causing the synergy, a series of dispersions were prepared for UVR absorption analyses. Table I-A summarizes the sample ID, the in-vitro SPF data and the UVA1 wavelength at which 0.5 absorbance units occurred. The former measurement provides a relative difference of the magnitude of UVR absorption. The latter measurement becomes important when evaluating the breadth of UVR absorption. The data clearly showed that not only does Kraton enhance the absorption activity of ZnO, but individually, Solastay (SS) does as well. Surprisingly, and more importantly, the presence of the combination of Kraton and Solastay together with ZnO showed a significant increase in both in-vitro SPF magnitude and UVA1 breadth of absorption, much greater than what would be expected based on the corresponding values for each component individually.

TABLE I-A

UVR Absorption Responses of ZnO in Kraton/Solastay Carrier Oil Dispersions

| Sample ID | Ingredients | Ratio | in-vitro SPF (units) | UVA1 (λ nm @0.5 abs) |
|---|---|---|---|---|
| 3043-3-15 | IPM/ZnO | 4.0/1.0 | 3 ± 0 STD | — |
| 3043-3-1 | OS | 4.0 (Neat) | 14 ± 0 STD | — |
| 3043-3-2 | OS/K | 3.8/0.2 | 14 ± 1 STD | — |
| 3043-3-6 | OS/K/ZnO | 3.8/0.2/1.0 | 170 ± 5 STD | 384.0 |
| 3043-3-14 | IPM/SS | 4.0/0.4 | 21 ± 3 STD | 380.0 |
| 3043-3-9 | OS/SS | 4.0/0.4 | 117 ± 7 STD | 383.5 |
| 3043-3-11 | OS/SS/ZnO | 4.0/0.4/1.0 | 258 ± 6 STD | 393.0 |
| 3043-3-12 | OS/K/SS/ZnO | 3.8/0.2/0.4/1.0 | 372 ± 10 STD | 397.0 |

Dose: 1.0 mg/cm² Clear Quartz Glass Slide

In using the data in Table I-A above, the unexpected synergy is evaluated from two different perspectives. Through the various dispersion combinations described in Table 1-B below, the theoretical expected in-vitro SPF values were 287 for Scenario 1, and 272 units for Scenario 2. These values were significantly lower than the observed in-vitro SPF value of 372 units for the presence of the combination of Kraton and Solastay with ZnO in a carrier oil dispersion.

TABLE I-B

UV Absorption Synergy of
ZnO in Kraton/Solastay Carrier Oil Dispersions

| Sample ID | Ingredients | Ratio | in-vitro SPF (units) | |
|---|---|---|---|---|
| Synergy Scenario 1 | | | | |
| 3043-3-6 | OS/K/ZnO | 3.8/0.2/1.0 | 170 ± 5 STD | |
| 3043-3-9 | OS/SS | 4.0/0.4 | 117 ± 7 STD | |
| | OS/K/SS/ZnO | 3.8/0.2/0.4/1.0 | 287 | Theoretical |
| 3043-3-12 | OS/K/SS/ZnO | 3.8/0.2/0.4/1.0 | 372 ± 10 STD | Observed |
| Synergy Scenario 2 | | | | |
| 3043-3-2 | OS/K | 3.8/0.2 | 14 ± 1 STD | |
| 3043-3-11 | OS/SS/ZnO | 4.0/0.4/1.0 | 258 ± 6 STD | |
| | OS/K/SS/ZnO | 3.8/0.2/0.4/1.0 | 272 | Theoretical |
| 3043-3-12 | OS/K/SS/ZnO | 3.8/0.2/0.4/1.0 | 372 ± 10 STD | Observed |

Dose: 1.0 mg/cm$^2$ Clear Quartz Glass Substrate

Study 2

A second study was performed to characterize the interaction of ZnO and ZnO-GEM complexes with Kraton and Solastay in carrier oil dispersions. The GEM stands for Gelling Electrostatic Matrix, whereby an alkyl silicone ethoxylated polymer such as Siltech J208-812 attaches itself via electrostatic interaction to the ZnO crystal lattice structure, thereby forming a lowest free energy complex. The complex is designated as ZnO-812. The dose of 0.55 mg/cm2 on PMMA substrate was selected for this and future studies so that the data range would fall below the maximum absorbance range limit of the instrument. The isopropyl myristate (IPM) and Cosmosurf CE100 (CE) neat materials listed in Table II-A had no UVR absorption activity on their own, and are thus used as q.s. diluents to maintain the remaining ingredient ratios. Key observations were as follows:

1. The GEM complex of ZnO-812 absorbed more UVR than plain ZnO. This is an unexpected result, as silicone surfactant exhibited essentially no UVR attenuation on its own.

2. Solastay adjuvated UVR attenuation capability of both ZnO-612 and ZnO-812. The amount of the increase in UVR attenuation for the ZnO-612 and ZnO-812 complexes was unexpected based on the UVR values for the individual compounds.

3. Kraton/Solastay combination synergistically adjuvated UVR attenuation (magnitude and breadth) of both ZnO, ZnO-612, and ZnO-812. This is unexpected, since Kraton has very little UVR attenuation ability on its own.

4. CE100 further maximized UVR attenuation capability of ZnO, ZnO-612, and ZnO-812 with and without Kraton and Solastay. Again, this is very much unexpected, since as shown, CE100 has almost no UVR attenuation ability on its own.

TABLE II-A

UVR Absorption Responses of
ZnO and ZnO-812 in Kraton/Solastay Carrier Oil Dispersions

| Sample ID | Ingredients | Ratio | in-vitro SPF (units) | UVA1 ($\lambda$ nm@0.5 abs) |
|---|---|---|---|---|
| 3088-76-1 | IPM | Neat | 1 ± 0 STD | — |
| 0031-17-26 | IPM-K (5% gel) | Neat | 1 ± 0 STD | — |
| 3088-72-1 | ZnO | Neat | 4 ± 0 STD | 375.5 |
| 3088-72-2 | IPM/ZnO | 4.0/1.0 | 4 ± 0 STD | 376.5 |
| 0031-17-28 | IPM/ZnO-812 | 4.0/1.0 | 7 ± 0 STD | 378.5 |
| 3088-75-11 | IPM/OS | 4.0/1.0 | 7 ± 0 STD | — |
| 3088-74-17 | IPM/SS | 4.5/0.5 | 12 ± 0 STD | 372.0 |
| 3088-72-3 | IPM/OS-K/ZnO | 3.0/1.0/1.0 | 17 ± 1 STD | 377.0 |
| 3088-72-16 | IPM/ZnO/SS | 3.5/1.0/0.5 | 31 ± 1 STD | 386.5 |
| 3088-75-9 | IPM/ZnO-812/SS | 3.5/1.0/0.5 | 52 ± 3 STD | 388.0 |
| 3088-72-4 | IPM/OS-K/ZnO/SS | 2.5/1.0/1.0/0.5 | 105 ± 3 STD | 389.0 |
| 3088-75-10 | IPM/OS-K/ZnO-812/SS | 2.5/1.0/1.0/0.5 | 129 ± 4 STD | 390.5 |
| 3088-75-8 | CE/OS-K/ZnO-812/SS | 2.5/1.0/1.0/0.5 | 156 ± 10 STD | 393.5 |
| 3088-75-7 | CE/OS/ZnO-812/SS | 2.5/1.0/1.0/0.5 | 133 ± 6 STD | 391.0 |
| 3088-72-18 | CE/OS/ZnO/SS | 2.5/1.0/1.0/0.5 | 64 ± 2 STD | 389.0 |
| 3088-75-6 | CE/ZnO-812/SS | 3.5/1.0/0.5 | 44 ± 2 STD | 390.0 |
| 3088-75-5 | CE/OS-K/ZnO-812 | 3.0/1.0/1.0 | 44 ± 2 STD | 380.0 |
| 3088-75-4 | CE/OS/ZnO-812 | 3.0/1.0/1.0 | 22 ± 0 STD | 377.5 |
| 3088-75-3 | CE/ZnO-812 | 4.0/1.0 | 17 ± 1 STD | 380.0 |
| 0008-85-6 | CE/SS | 4.5/0.5 | 21 ± 1 STD | 381.0 |
| 0008-87-2 | CE/OS | 4.0/1.0 | 8 ± 0 STD | — |
| 0008-104-1 | CE/ZnO | 4.0/1.0 | 5 ± 0 STD | 376.0 |
| 0008-85-3 | CE-K | Incompatible | — | — |
| 0008-85-1 | CE | Neat | 1 ± 0 STD | — |
| 0008-106 | SS | Neat* | 4 ± 0 STD | 373.0 |

Dose: 0.55 mg/cm$^2$ PMMA substrate
*Solastay target dose on PMMA substrate was 0.11 mg//cm$^2$ PMMA substrate to account for ratio proportion.

The enhanced UVR absorption responses of ZnO-812 versus the plain ZnO are clearly shown in FIG. 1. Also, the synergy between the ZnO-812 and the Kraton/Solastay combination significantly enhanced the UVR absorption responses.

Table II-B summarizes three different scenarios that establish the synergy of ZnO with Kraton/Solastay in a carrier oil dispersion. The observed in-vitro SPF value of 105 is significantly higher than the theoretical in-vitro SPF values of 24, 29, and 48.

TABLE II-B

UV Absorption Synergy of ZnO in Kraton/Solastay Polar Dispersions

| Sample ID | Ingredients | Ratio | in-vitro SPF (units) | |
|---|---|---|---|---|
| Scenario 1 | | | | |
| 0031-17-26 | IPM-K (5% gel) | Neat | 1 ± 0 STD | |
| 3088-72-2 | IPM/ZnO | 4.0/1.0 | 4 ± 0 STD | |
| 3088-75-11 | IPM/OS | 4.0/1.0 | 7 ± 0 STD | |
| 3088-74-17 | IPM/SS | 4.5/0.5 | 12 ± 0 STD | |
| | IPM/OS-K/ZnO/SS | 2.5/1.0/1.0/0.5 | 24 | Theoretical |
| 3088-72-4 | IPM/OS-K/ZnO/SS | 2.5/1.0/1.0/0.5 | 105 ± 3 STD | Observed |
| Scenario 2 | | | | |
| 3088-72-3 | IPM/OS-K/ZnO | 3.0/1.0/1.0 | 17 ± 1 STD | |
| 3088-74-17 | IPM/SS | 4.5/0.5 | 12 ± 0 STD | |
| | IPM/OS-K/ZnO/SS | 2.5/1.0/1.0/0.5 | 29 | Theoretical |
| 3088-72-4 | IPM/OS-K/ZnO/SS | 2.5/1.0/1.0/0.5 | 105 ± 3 STD | Observed |
| Scenario 3 | | | | |
| 3088-72-3 | IPM/OS-K/ZnO | 3.0/1.0/1.0 | 17 ± 1 STD | |
| 3088-72-16 | IPM/ZnO/SS | 3.5/1.0/0.5 | 31 ± 1 STD | |
| | IPM/OS-K/ZnO/SS | 2.5/1.0/1.0/0.5 | 48 | Theoretical |
| 3088-72-4 | IPM/OS-K/ZnO/SS | 2.5/1.0/1.0/0.5 | 105 ± 3 STD | Observed |

Dose: 0.55 mg/cm$^2$ PMMA substrate

Table II-C summarizes two different scenarios that establish the synergy of ZnO-812 with Kraton/Solastay in a carrier oil dispersion. The observed in-vitro SPF value of 129 is significantly higher than the theoretical in-vitro SPF values of 27 and 60.

TABLE II-C

UV Absorption Synergy of ZnO-812 in Kraton/Solastay Carrier Oil Dispersions

| Sample ID | Ingredients | Ratio | in-vitro SPF (units) | |
|---|---|---|---|---|
| Scenario 1 | | | | |
| 0031-17-26 | IPM-K (5% gel) | Neat | 1 ± 0 STD | |
| 3088-72-2 | IPM/ZnO-812 | 4.0/1.0 | 7 ± 0 STD | |
| 3088-75-11 | IPM/OS | 4.0/1.0 | 7 ± 0 STD | |
| 3088-74-17 | IPM/SS | 4.5/0.5 | 12 ± 0 STD | |
| | IPM/OS-K/ZnO-812/SS | 2.5/1.0/1.0/0.5 | 27 | Theoretical |
| 3088-72-4 | IPM/OS-K/ZnO-812/SS | 2.5/1.0/1.0/0.5 | 129 ± 3 STD | Observed |

TABLE II-C-continued

UV Absorption Synergy of ZnO-812 in Kraton/Solastay Carrier Oil Dispersions

| Sample ID | Ingredients | Ratio | in-vitro SPF (units) | |
|---|---|---|---|---|
| Scenario 2 | | | | |
| 0031-17-26 | IPM-K (5% gel) | Neat | 1 ± 0 STD | |
| 3088-75-11 | IPM/OS | 4.0/1.0 | 7 ± 0 STD | |
| 3088-75-9 | IPM/ZnO-812/SS | 3.5/1.0/0.5 | 52 ± 3 STD | |
| | IPM/OS-K/ZnO-812/SS | 2.5/1.0/1.0/0.5 | 60 | Theoretical |
| 3088-72-4 | IPM/OS-K/ZnO-812/SS | 2.5/1.0/1.0/0.5 | 129 ± 3 STD | Observed |

Dose: 0.55 mg/cm$^2$ PMMA substrate

Table II-D summarizes two different scenarios that establish the synergy of ZnO-812 with Kraton/Solastay in a CE100 carrier oil dispersion. The observed in-vitro SPF value of 156 is significantly higher than the theoretical in-vitro SPF values of 47 and 65.

TABLE II-D

UV Absorption Synergy of ZnO-812 and CE100/Kraton/Solastay Carrier Oil Dispersions

| Sample ID | Ingredients | Ratio | in-vitro SPF (units) | |
|---|---|---|---|---|
| Scenario 1 | | | | |
| 0008-85-1 | CE | Neat | 1 ± 0 STD | |
| 0008-85-3 | CE-K | Incompatible | — | |
| 3088-75-3 | CE/ZnO-812 | 4.0/1.0 | 17 ± 1 STD | |
| 0008-87-2 | CE/OS | 4.0/1.0 | 8 ± 0 STD | |
| 0008-85-6 | CE/SS | 4.5/0.5 | 21 ± 1 STD | |
| | CE/OS-K/ZnO-812/SS | 2.5/1.0/1.0/0.5 | 47 | Theoretical |
| 3088-75-8 | CE/OS-K/ZnO-812/SS | 2.5/1.0/1.0/0.5 | 156 ± 10 STD | Observed |
| Scenario 2 | | | | |
| 0008-85-6 | CE/SS | 4.5/0.5 | 21 ± 1 STD | |
| 3088-75-5 | CE/OS-K/ZnO-812 | 3.0/1.0/1.0 | 44 ± 2 STD | |
| | CE/OS-K/ZnO-812/SS | 2.5/1.0/1.0/0.5 | 65 | Theoretical |
| 3088-75-8 | CE/OS-K/ZnO-812/SS | 2.5/1.0/1.0/0.5 | 156 ± 10 STD | Observed |

Dose: 0.55 mg/cm$^2$ PMMA substrate

Table II-E shows another unexpected synergy with Solastay in combination with CE100 versus the Solastay dispersed in IPM. Both CE100 and IPM are transparent to UVA, and therefore it is remarkable that the Solastay in-vitro SPF magnitude would increase by 11 units, almost double, upon dispersion in CE100 versus IPM.

TABLE II-E

UV Absorption Synergy of Solastay/CE100 Dispersion versus Solastay/IPM

| Sample ID | Ingredients | Ratio | in-vitro SPF (units) | |
|---|---|---|---|---|
| Scenario 1 | | | | |
| 3088-76-1 | IPM | Neat | 1 ± 0 STD | |
| 0008-106 | SS | Neat * | 4 ± 0 STD | |
| | IPM/SS | 4.5/0.5 | 5 | Theoretical |

TABLE II-E-continued

UV Absorption Synergy of Solastay/CE100 Dispersion versus Solastay/IPM

| Sample ID | Ingredients | Ratio | in-vitro SPF (units) | |
|---|---|---|---|---|
| 3088-74-17 | IPM/SS | 4.5/0.5 | 12 ± 0 STD | Observed |
| 0008-85-1 | CE | Neat | 1 ± 0 STD | |
| 0008-106 | SS | Neat * | 4 ± 0 STD | |
| | CE/SS | 4.5/0.5 | 5 | Theoretical |
| 0008-85-6 | CE/SS | 4.5/0.5 | 21 ± 1 STD | Observed |

Study 3

The purpose of this study was to further characterize the interaction of CE100 with ZnO and the ZnO-GEMs prepared with J208-612 and J208-812. J208-612 is slightly more water soluble, with 6 sites containing C12 groups, and 4 sites containing eight moles of ethoxylation. J208-812 is completely hydrophobic with 8 sites containing C12 groups, and 2 sites containing eight moles of ethoxylation. Kraton is not directly compatible with CE100, and therefore not included in this study. The carrier oil, octisalate, is also absent. The data in Table III-A below clearly shows the increasing UVR absorption capability of the ZnO-GEMs versus plain ZnO. Also, the influence of Solastay to adjuvate UVR absorption capability of the ZnO-GEM's is noted.

TABLE III-A

UVR Absorption Responses of ZnO and ZnO-GEM in CE/Solastay Dispersions

| Sample ID | Ingredients | Ratio | in-vitro SPF (units) | UVA1 λ nm@0.5 abs |
|---|---|---|---|---|
| 0008-85-1 | CE100 | Neat | 1 ± 0 STD | — |
| 0008-104-1 | CE100/ZnO | 4.0/1.0 | 5 ± 0 STD | 376 |
| 0008-104-2 | CE100/ZnO-612 | 4.0/1.0 | 9 ± 0 STD | 378 |
| 0008-85-11 | CE100/ZnO-812 | 4.0/1.0 | 16 ± 1 STD | 380 |
| 0008-85-6 | CE100/SS | 4.5/0.5 | 21 ± 1 STD | 381 |
| 0008-104-3 | CE100/ZnO/SS | 3.5/1.0/0.5 | 47 ± 1 STD | 388 |
| 0008-104-4 | CE100/ZnO-612/SS | 3.5/1.0/0.5 | 57 ± 0 STD | 389 |
| 0008-85-12 | CE100/ZnO-812/SS | 3.5/1.0/0.5 | 70 ± 2 STD | 392 |

Dose: 0.55 mg/cm$^2$ PMMA substrate

Table III-B establishes the synergy of the ZnO-GEMs with Solastay in CE100 dispersion. The observed in-vitro SPF value of 57 was significantly higher than the theoretical in-vitro SPF value of 30 for ZnO-612. The observed in-vitro SPF value of 70 was significantly higher than the theoretical in-vitro SPF value of 37 for ZnO-812.

TABLE III-B

UV Absorption Synergy of ZnO and ZnO-GEM in CE100/Solastay Dispersions

| Sample ID | Ingredients | Ratio | in-vitro SPF (units) | |
|---|---|---|---|---|
| | | Synergy with ZnO-612 | | |
| 0008-104-2 | CE100/ZnO-612 | 4.0/1.0 | 9 ± 0 STD | |
| 0008-85-6 | CE100/SS | 4.5/0.5 | 21 ± 1 STD | |
| | CE100/ZnO-612/SS | 3.5/1.0/0.5 | 30 | Theoretical |
| 0008-104-4 | CE100/ZnO-612/SS | 3.5/1.0/0.5 | 57 ± 0 STD | Observed |

TABLE III-B-continued

UV Absorption Synergy of ZnO and ZnO-GEM in CE100/Solastay Dispersions

| Sample ID | Ingredients | Ratio | in-vitro SPF (units) | |
|---|---|---|---|---|
| | | Synergy with ZnO-812 | | |
| 0008-85-11 | CE100/ZnO-812 | 4.0/1.0 | 16 ± 1 STD | |
| 0008-85-6 | CE100/SS | 4.5/0.5 | 21 ± 1 STD | |
| | CE100/ZnO-812/SS | 3.5/1.0/0.5 | 37 | Theoretical |
| 0008-85-12 | CE100/ZnO-812/SS | 3.5/1.0/0.5 | 70 ± 2 STD | Observed |

Dose: 0.55 mg/cm$^2$ PMMA substrate

Study 4

Figure 2:
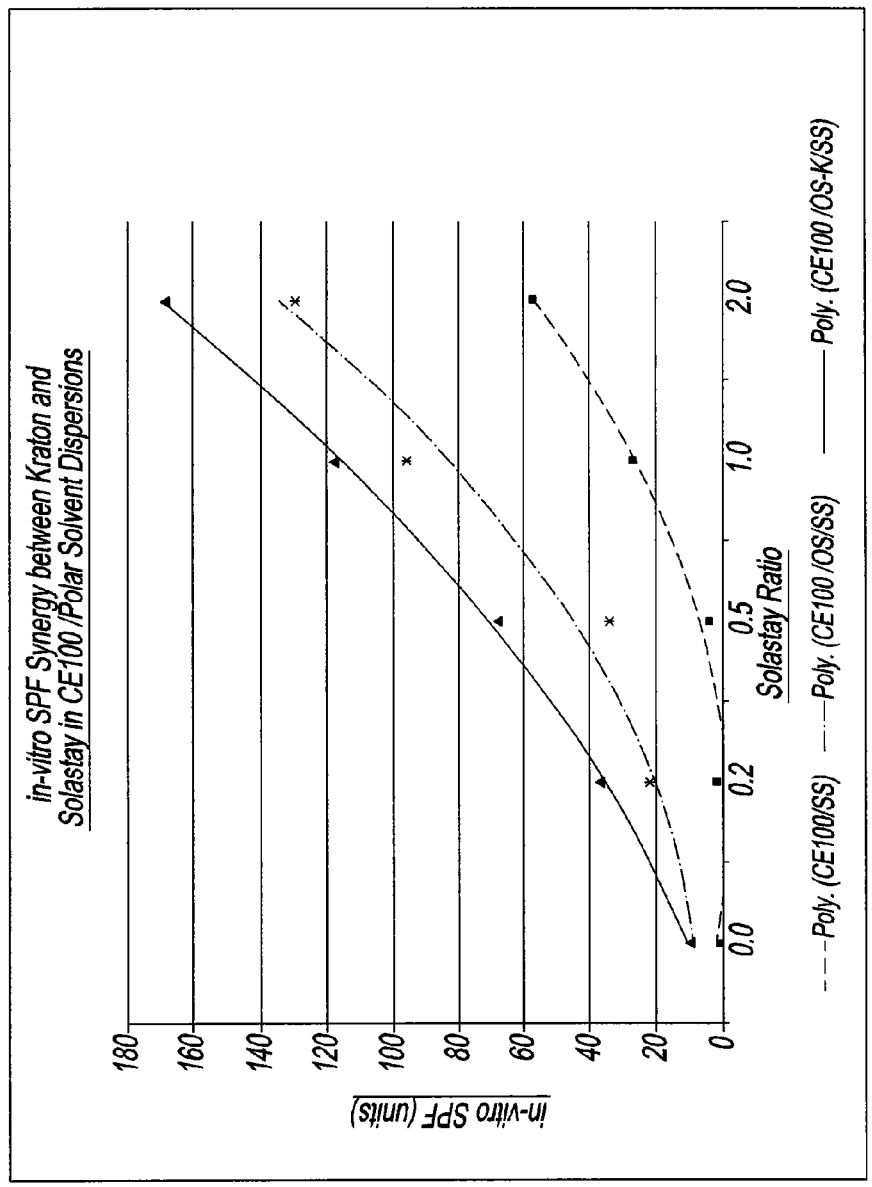

The purpose of this study was to explore the interrelationship between CE100, Kraton and Solastay, since it had been observed that sometimes dispersions were uniform and other times a non-uniform dispersion with agglomerate would occur. The first set of data in Table IV shows increasing in-vitro SPF magnitude as Solastay concentration increased, which was expected. Since CE100 had no UV absorption capability, the in-vitro SPF contribution was provided by the Solastay material. In previous experiments, the CE100/OS-K/SS ratio was 3.5:1.0:0.5. In those experiments, it appeared that the Kraton gellant migrated from octisalate to the preferred, relatively more hydrocarbon alkyl chains on the CE100, and thus, non-uniform agglomerate formed. To change dispersion dynamics and achieve a uniform dispersion, the OS-K content in the ratio was increased. Uniform dispersions were obtained and satisfactorily spread on the PMMA substrate. The second data set in Table IV shows the impact of the UV absorbing compound, octisalate, had on increasing the in-vitro SPF magnitude of the CE100/SS dispersion. The unexpected results for the absorption responses shown in the third data set came from the synergistic impact Kraton had with Solastay. The control sample of Kraton added to CE100/OS had no impact on increasing in-vitro SPF, as indicated by the same value of 10 units. However, a comparison of CE100/OS/SS dispersions to the corresponding CE100/OS-K/SS dispersions showed synergistic absorption responses at each ratio, as shown in FIG. 2. Surprisingly, the in-vitro SPF values for the samples containing Solastay fit a polynomial curve as opposed to a linear regression.

TABLE IV

UVR Absorption Responses of Kraton/Solastay in CE100 and CE100/Carrier Oil Dispersions

| | Ingredient Ratio | | | | Absorption Response | |
|---|---|---|---|---|---|---|
| Sample ID | CE100 | OS | OS/K | SS | in-vitro SPF (units) | UVA1 (λnm@0.5 abs) |
| 0008-85-1 | 10.0 | — | — | — | 1 ± 0 STD | |
| 0008-96-1 | 9.8 | — | — | 0.2 | 2 ± 0 STD | — |
| 0008-96-2 | 9.8 | — | — | 0.5 | 4 ± 0 STD | 364.0 |
| 0008-96-3 | 9.0 | — | — | 1.0 | 27 ± 0 STD | 382.0 |
| 0008-96-4 | 8.0 | — | — | 2.0 | 57 ± 2 STD | 389.5 |
| 0008-96-13 | 5.0 | 5.0 | — | 0.0 | 10 ± 1 STD | — |
| 0008-96-5 | 4.8 | 5.0 | — | 0.2 | 22 ± 1 STD | 340.0 |
| 0008-96-6 | 4.5 | 5.0 | — | 0.5 | 34 ± 4 STD | 368.0 |
| 0008-96-7 | 4.0 | 5.0 | — | 1.0 | 96 ± 4 STD | 382.0 |
| 0008-96-8 | 3.0 | 5.0 | — | 2.0 | 130 ± 4 STD | 388.0 |
| 0008-96-14 | 5.0 | — | 5.0 | 0.0 | 10 ± 1 STD | — |
| 0008-96-9 | 4.8 | — | 5.0 | 0.2 | 37 ± 4 STD | 382.0 |
| 0008-96-10 | 4.5 | — | 5.0 | 0.5 | 68 ± 4 STD | 386.0 |

TABLE IV-continued

UVR Absorption Responses of
Kraton/Solastay in CE100 and CE100/Carrier Oil Dispersions

| Sample ID | Ingredient Ratio | | | | Absorption Response | |
|---|---|---|---|---|---|---|
| | CE100 | OS | OS/K | SS | in-vitro SPF (units) | UVA1 (λnm@0.5 abs) |
| 0008-96-11 | 4.0 | — | 5.0 | 1.0 | 118 ± 4 STD | 386.5 |
| 0008-96-12 | 3.0 | — | 5.0 | 2.0 | 169 ± 4 STD | 390.0 |

Dose: 0.55 mg/cm² PMMA substrate

Study 5

It is known that solvent polarity affects the UV absorption spectrum of sunscreen active materials, in that generally increasing polarity enhances sunscreen performance.

It is also known that there is an upper limit and the effect is system dependent. Therefore, knowledge of solvent polarity based on dielectric constant, Table V, helps to understand simple systems such as the dispersions listed below.

TABLE V

Solvent Polarity

| Solvent | Dielectric Constant |
|---|---|
| Mineral Oil | 2.30 |
| Isopropyl Myristate | 3.25 |
| Ethylhexyl Benzoate | 4.61 |
| Butyloctyl Salicylate | 5.27 |
| Ethylhexyl Salicylate | 6.25 |

The purpose of Study 5 was to investigate the UV absorption responses of two ZnO-GEMs versus plain ZnO as a function of solvent polarity. The data in Table VI-a showed the following trends in the absorption response for in-vitro SPF:

1. The GEM materials, J208-612 and 812 were transparent to UVR, and thus had no effect on in-vitro SPF magnitude.
2. The ZnO-GEM materials attenuated UVR more so than plain ZnO in the aromatic carrier oils of BHB and OS. Thus increases in in-vitro SPF magnitudes were observed, and were synergistic because it was the GEM materials complexed with ZnO that caused the enhancement in UVR activity.
3. ZnO-812 attenuated UVR more efficiently than ZnO-612.

TABLE VI-A

ZnO and ZnO-GEMs in Carrier Oil Dispersions
Absorption Response of in-Vitro SPF

| Sample | Ratio | in-vitro SPF (units) | | | |
|---|---|---|---|---|---|
| | | IPM | EB | BHB | OS |
| Solvent | Neat | 1 ± 0 STD | 1 ± 0 STD | 12 ± 0 STD | 12 ± 0 STD |
| +J208-612 | 4.9/0.1 | 1 ± 0 STD | 1 ± 0 STD | 12 ± 0 STD | 13 ± 0 STD |
| +J208-812 | 4.9/0.1 | 1 ± 0 STD | 1 ± 0 STD | 13 ± 0 STD | 12 ± 0 STD |
| +ZnO | 4.0/1.0 | 8 ± 1 STD | 14 ± 1 STD | 63 ± 2 STD | 76 ± 0 STD |
| +ZnO-612 | 4.0/1.0 | 7 ± 0 STD | 13 ± 1 STD | 71 ± 1 STD | 84 ± 2 STD |
| +ZnO-812 | 4.5/0.5 | — | — | — | 41 ± 2 STD |
| +ZnO-812 | 4.0/1.0 | 7 ± 0 STD | 14 ± 1 STD | 85 ± 4 STD | 94 ± 1 STD |
| +ZnO-812 | 3.0/2.0 | — | — | — | 118 ± 3 STD |

Dose: 0.55 mg/cm² PMMA substrate

Figure 3:
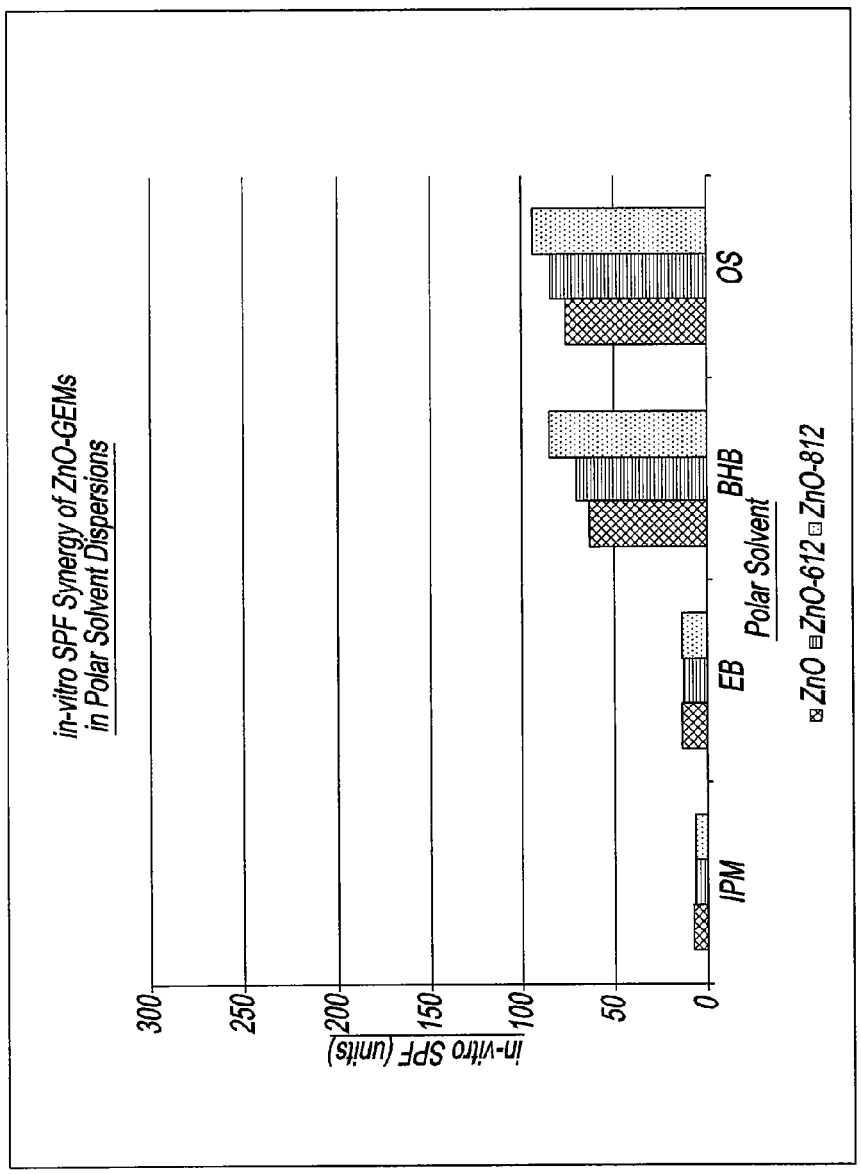

FIG. 3 depicts the trend in in-vitro SPF of ZnO and the ZnO-GEM materials as they were influenced by solvent polarity. It can be seen clearly that the presence of a Gelling Electrostatic Matrix (GEM) enhanced the UV absorption capability of ZnO.

Figure 5:
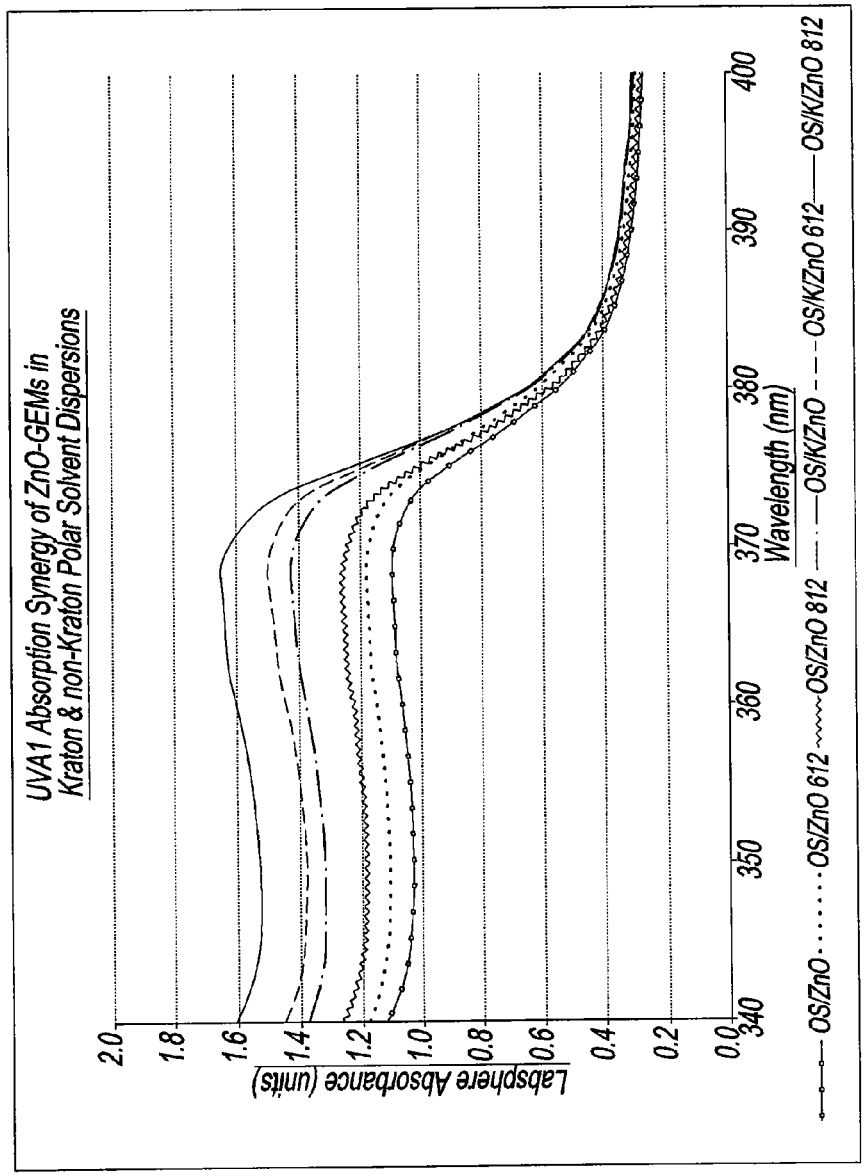

Table VI-B summarizes the UVA1 absorption response data by determining the wavelength at 0.5 absorbance units in the 340-400 nm region. Although the wavelengths @ 0.5 abs were similar between the plain ZnO and the ZnO-GEMs, it is in FIG. 5 that the differences in UVA1 magnitude are shown amongst the dispersions.

TABLE VI-B

ZnO and ZnO-GEMs in Carrier Oil Dispersions
Absorption Response of UVA1

| Sample | Ratio | UVA1 (λ nm @0.5 abs) | | | |
|---|---|---|---|---|---|
| | | IPM | EB | BHB | OS |
| Solvent | Neat | — | — | — | — |
| +J208-612 | 4.9/0.1 | — | — | — | — |
| +J208-812 | 4.9/0.1 | — | — | — | — |
| +ZnO | 4.0/1.0 | 379.5 | 381.0 | 379.5 | 381.0 |
| +ZnO-612 | 4.0/1.0 | 378.0 | 381.5 | 380.0 | 382.0 |
| +ZnO-812 | 4.5/0.5 | — | — | — | 375.0 |
| +ZnO-812 | 4.0/1.0 | 378.5 | 381.0 | 380.0 | 381.5 |
| +ZnO-812 | 3.0/2.0 | — | — | — | 384.0 |

Dose: 0.55 mg/cm² PMMA substrate

Study 6

Figure 4:
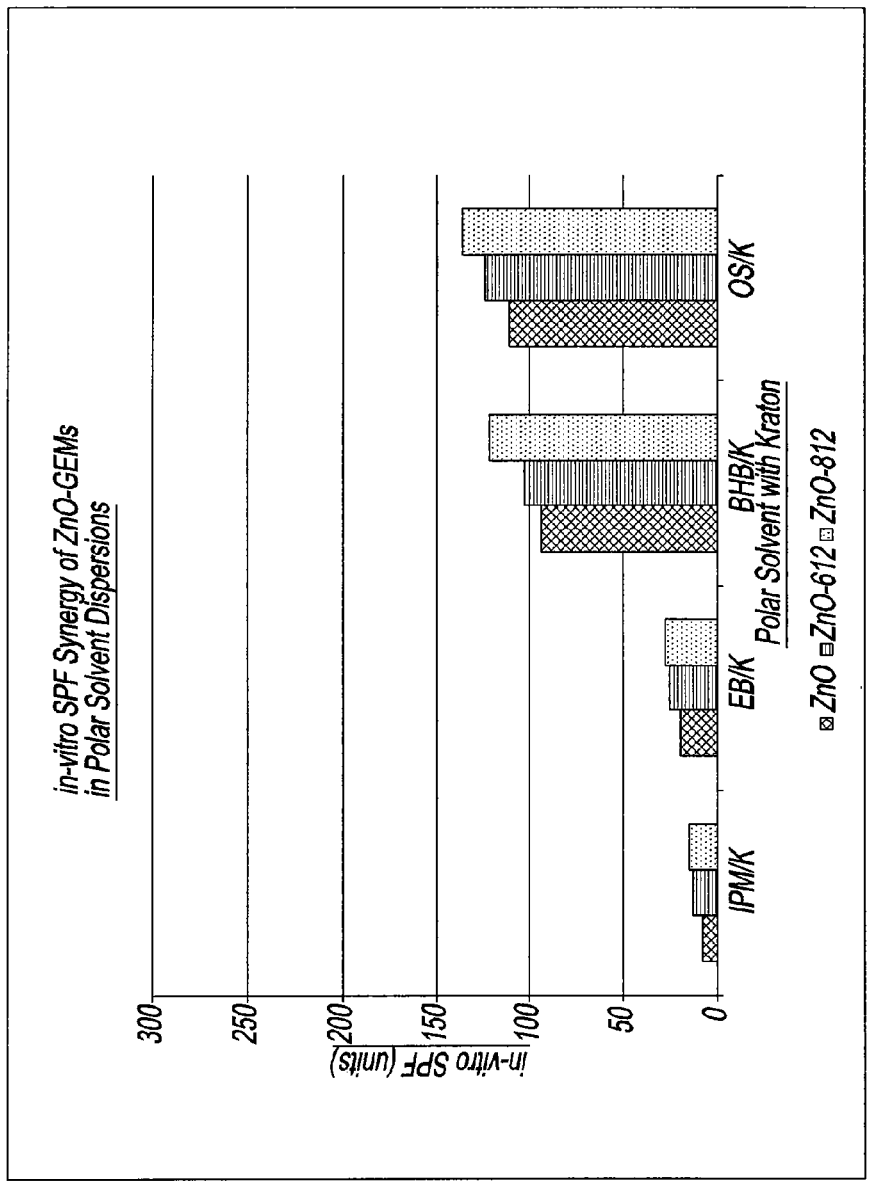

This study was a continuation of Study 5 whereby the effects of the addition of Kraton to the plain ZnO and the ZnO-Gem dispersions were investigated. The carrier oils were gelled with 5% Kraton, which was transparent to UVR. The in-vitro SPF data summarized in Table VII-A were the same as those noted above. However, the magnitudes of absorption for the Kraton containing dispersions were unexpectedly higher and clearly illustrated in FIG. 4.

TABLE VII-A

ZnO and ZnO-GEMs in Kraton/Carrier Oil Dispersions
Absorption Response of in-vitro SPF

| Sample | Ratio | in-vitro SPF (units) | | | |
|---|---|---|---|---|---|
| | | IPM/K | EB/K | BHB/K | OS/K |
| Solvent | Neat | 1 ± 0 STD | 1 ± 0 STD | 13 ± 0 STD | 12 ± 0 STD |
| +J208-612 | 4.9/0.1 | 1 ± 0 STD | 1 ± 0 STD | 12 ± 0 STD | 13 ± 0 STD |
| +J208-812 | 4.9/0.1 | 1 ± 0 STD | 1 ± 0 STD | 13 ± 0 STD | 12 ± 0 STD |
| +ZnO | 4.0/1.0 | 8 ± 0 STD | 19 ± 1 STD | 93 ± 2 STD | 110 ± 2 STD |
| +ZnO-612 | 4.0/1.0 | 13 ± 1 STD | 25 ± 2 STD | 102 ± 0 STD | 123 ± 3 STD |
| +ZnO-812 | 4.5/0.5 | — | — | — | 64 ± 3 STD |
| +ZnO-812 | 4.0/1.0 | 15 ± 1 STD | 27 ± 1 STD | 121 ± 2 STD | 135 ± 1 STD |
| +ZnO-812 | 3.0/2.0 | — | — | — | 151 ± 2 STD |

Dose: 0.55 mg/cm² PMMA substrate

The data in Table VII-B shows essentially the same behavior for UVA1 as noted in the previous study in that the wavelength at 0.5 absorbance units occurred nearly at the same point. It is in FIG. 5 that the increases in UVA1 absorbance from 340-380 nm were noticeably higher for the Kraton dispersions versus the non-Kraton dispersions. Since Kraton is transparent to UVR, the increases in UVA1 were synergistic for the combination with ZnO-GEM materials.

TABLE VII-B

ZnO and ZnO-GEMs in Kraton/Carrier Oil Dispersions
Absorption Response of UVA1

| Sample | Ratio | UVA1 (λ nm @0.5 abs) | | | |
|---|---|---|---|---|---|
| | | IPM/K | EB/K | BHB/K | OS/K |
| Solvent | Neat | — | — | — | — |
| +J208-612 | 4.9/0.1 | — | — | — | — |
| +J208-812 | 4.9/0.1 | — | — | — | — |
| +ZnO | 4.0/1.0 | 379.0 | 382.0 | 381.0 | 381.0 |
| +ZnO-612 | 4.0/1.0 | 381.0 | 383.5 | 381.0 | 382.5 |
| +ZnO-812 | 4.5/0.5 | — | — | — | 378.0 |
| +ZnO-812 | 4.0/1.0 | 381.5 | 382.0 | 382.0 | 382.5 |
| +ZnO-812 | 3.0/2.0 | — | — | — | 386.0 |

Dose: 0.55 mg/cm² PMMA substrate

Study 7

This study was also a continuation of Study 5 and focused on the addition of Solastay to the ZnO and ZnO-GEM carrier oil dispersions. It was important to note the baseline in-vitro SPF contribution of Solastay in the carrier oils as presented in Table VIII-A, and also note that the presence of the GEM materials J208-612 and 812 had no effect on in-vitro SPF. Interestingly, the non-aromatic as well as the aromatic carrier oils were showing significant, higher increases in in-vitro SPF versus those presented in Tables VI-A and VII-A.

TABLE VIII-A

ZnO and ZnO-GEMs in Solastay Carrier Oil Dispersions
Absorption Response of In-vitro SPF

| Sample | Ratio | in-vitro SPF (units) | | | |
|---|---|---|---|---|---|
| | | IPM | EB | BHB | OS |
| Solvent | Neat | 1 ± 0 STD | 1 ± 0 STD | 12 ± 0 STD | 12 ± 0 STD |
| +SS | 4.5/0.5 | 13 ± 1 STD | 21 ± 1 STD | 50 ± 2 STD | 65 ± 2 STD |
| +J208-612/SS | 4.4/0.1/0.5 | 13 ± 0 STD | 21 ± 2 STD | 53 ± 1 STD | 67 ± 1 STD |
| +J208-812/SS | 4.4/0.1/0.5 | 13 ± 1 STD | 22 ± 2 STD | 52 ± 2 STD | 67 ± 2 STD |
| +ZnO SS | 3.5/1.0/0.5 | 18 ± 1 STD | 51 ± 3 STD | 89 ± 2 STD | 117 ± 2 STD |
| +ZnO-612/SS | 3.5/1.0/0.5 | 23 ± 1 STD | 63 ± 2 STD | 152 ± 2 STD | 145 ± 4 STD |
| +ZnO-812/SS | 3.8/1.0/0.2 | — | — | — | 74 ± 2 STD |
| +ZnO-812/SS | 3.5/1.0/0.5 | 29 ± 0 STD | 73 ± 3 STD | 136 ± 4 STD | 167 ± 3 STD |
| +ZnO-812/SS | 3.0/1.0/1.0 | — | — | — | 201 ± 4 STD |

Dose: 0.55 mg/cm² PMMA substrate

Figure 6:
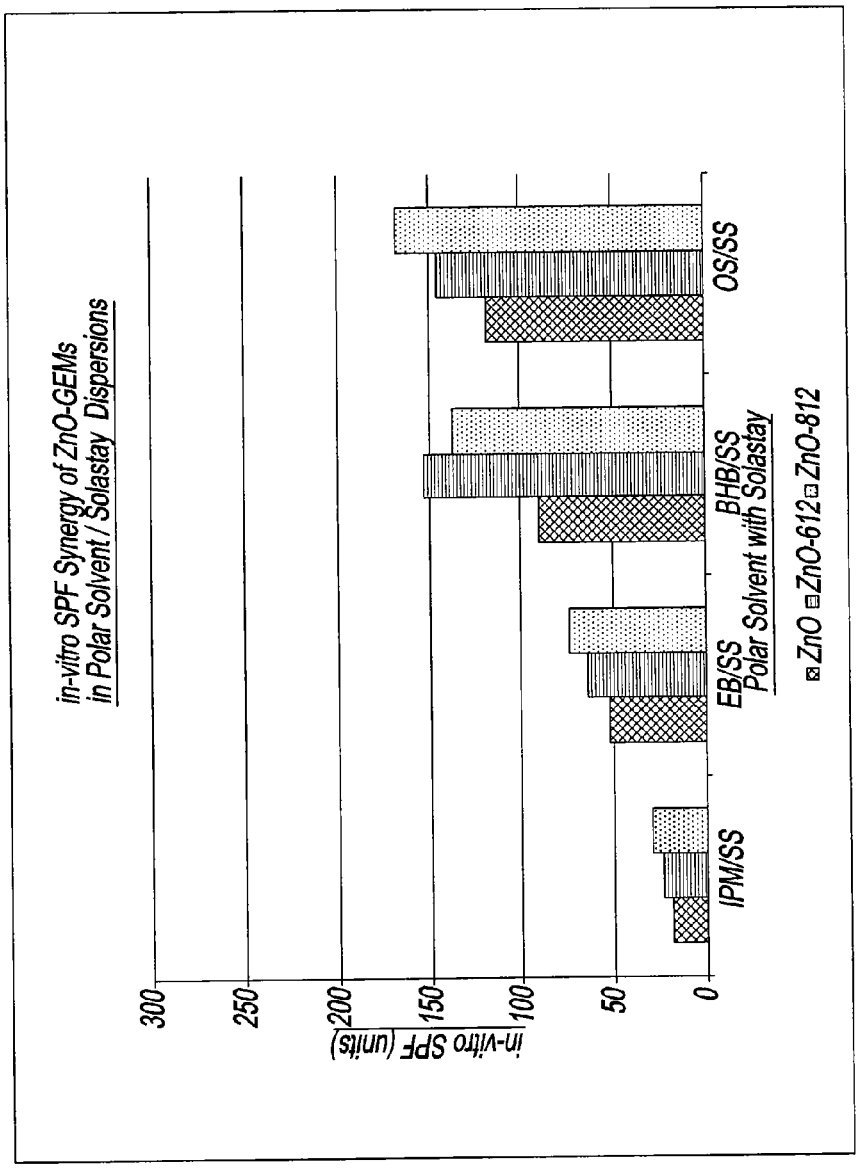

FIG. 6 shows the significant, synergistic increases in in-vitro SPF across the aromatic and non-aromatic carrier oils.

Figure 8:
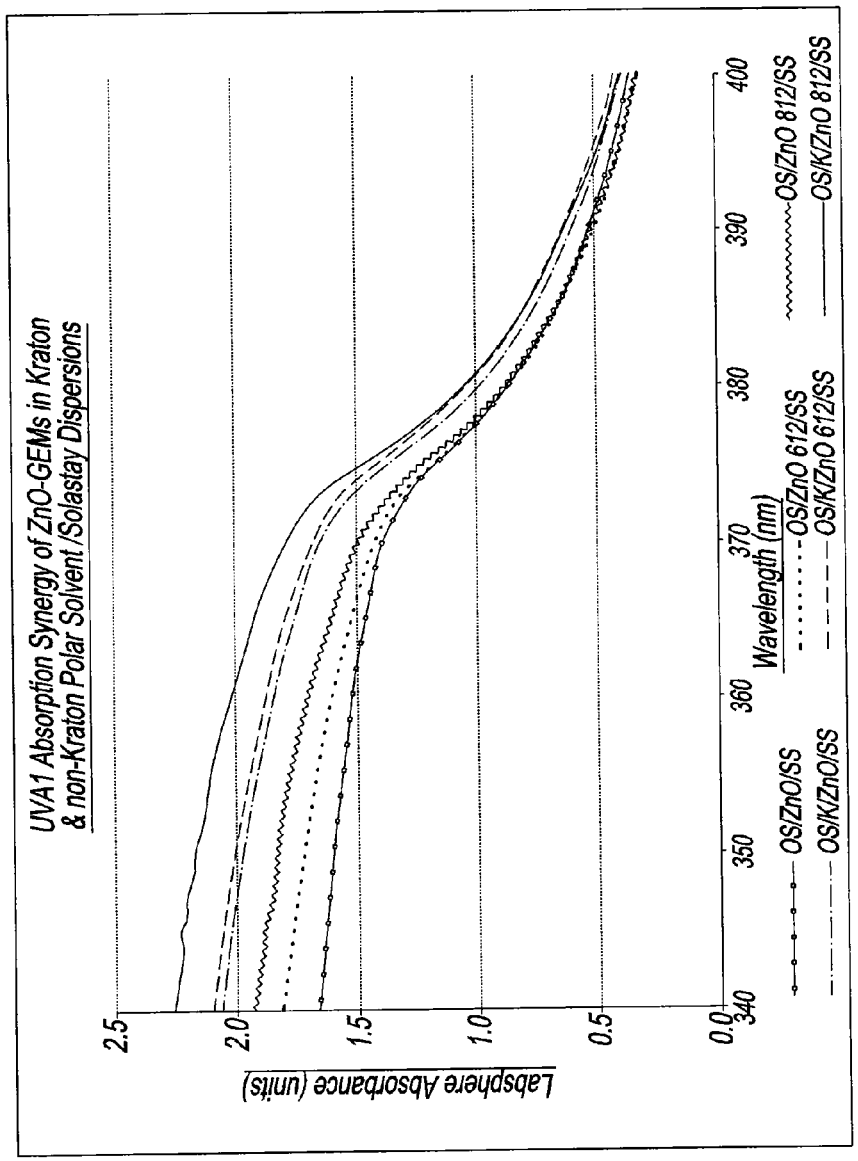

The UVA1 data summarized in Table VIII-B shows higher values for wavelengths at 0.5 absorbance units. However, the trend was the same as noted previously in that the UVA1 wavelength numbers @ 0.5 abs were similar between the plain ZnO and the ZnO-GEMs. As shown in FIG. 8, the synergistic differences in UVA1 magnitudes between the ZnO and the ZnO-GEMs became more apparent in the 340-370 nm region.

TABLE VIII-B

ZnO and ZnO-GEMs in Solastay Carrier Oil Dispersions
Absorption Response of UVA1

| Sample | Ratio | UVA1 (λ nm @0.5 abs) | | | |
|---|---|---|---|---|---|
| | | IPM | EB | BHB | OS |
| Solvent | Neat | — | — | — | — |
| +SS | 4.5/0.5 | 374.0 | 380.0 | 376.0 | 377.0 |
| +J208-612/SS | 4.4/0.1/0.5 | 374.0 | 381.0 | 375.5 | 378.5 |
| +J208-812/SS | 4.4/0.1/0.5 | 374.5 | 382.0 | 375.0 | 378.5 |
| +ZnO/SS | 3.5/1.0/0.5 | 381.5 | 393.0 | 387.0 | 391.5 |

TABLE VIII-B-continued

ZnO and ZnO-GEMs in Solastay Carrier Oil Dispersions
Absorption Response of UVA1

| | | UVA1 ($\lambda$ nm @0.5 abs) | | | |
|---|---|---|---|---|---|
| Sample | Ratio | IPM | EB | BHB | OS |
| +ZnO-612/SS | 3.5/1.0/0.5 | 385.0 | 397.0 | 391.5 | 390.0 |
| +ZnO-812/SS | 3.8/1.0/0.2 | — | — | — | 382.0 |
| +ZnO-812/SS | 3.5/1.0/0.5 | 384.0 | 394.0 | 389.0 | 390.5 |
| +ZnO-812/SS | 3.0/1.0/1.0 | — | — | — | 397.0 |

Dose: 0.55 mg/cm$^2$ PMMA substrate

Study 8

This Study was a continuation of Study 7 whereby the effects of the addition of Kraton to the ZnO and ZnO-GEM Solastay/carrier oil dispersions were investigated. The in-vitro SPF data in Table IX-A showed increasing magnitudes across the non-aromatic and aromatic carrier oils.

TABLE IX-A

ZnO and ZnO-GEMs in Kraton/Solastay Carrier Oil Dispersions
Absorption Response of In-vitro SPF

| | | in-vitro SPF (units) | | | |
|---|---|---|---|---|---|
| Sample | Ratio | IPM/K | EB/K | BHB/K | OS/K |
| Solvent | Neat | 1 ± 0 STD | 1 ± 0 STD | 13 ± 0 STD | 12 ± 0 STD |
| +SS | 4.5/0.5 | 22 ± 1 STD | 32 ± 0 STD | 61 ± 2 STD | 80 ± 1 STD |
| +J208-612/SS | 4.4/0.1/0.5 | 20 ± 1 STD | 32 ± 0 STD | 71 ± 2 STD | 81 ± 3 STD |
| +J208-812/SS | 4.4/0.1/0.5 | 22 ± 1 STD | 31 ± 1 STD | 71 ± 2 STD | 81 ± 3 STD |
| +ZnO/SS | 3.5/1.0/0.5 | 42 ± 1 STD | 92 ± 2 STD | 162 ± 6 STD | 214 ± 3 STD |
| +ZnO-612/SS | 3.5/1.0/0.5 | 56 ± 2 STD | 113 ± 3 STD | 181 ± 2 STD | 232 ± 2 STD |
| +ZnO-812/SS | 3.8/1.0/0.2 | — | — | — | 103 ± 3 STD |
| +ZnO-812/SS | 3.5/1.0/0.5 | 77 ± 7 STD | 131 ± 4 STD | 194 ± 2 STD | 255 ± 3 STD |
| +ZnO-812/SS | 3.0/1.0/1.0 | — | — | — | 304 ± 5 STD |

Dose: 0.55 mg/cm$^2$ PMMA substrate

Figure 7:
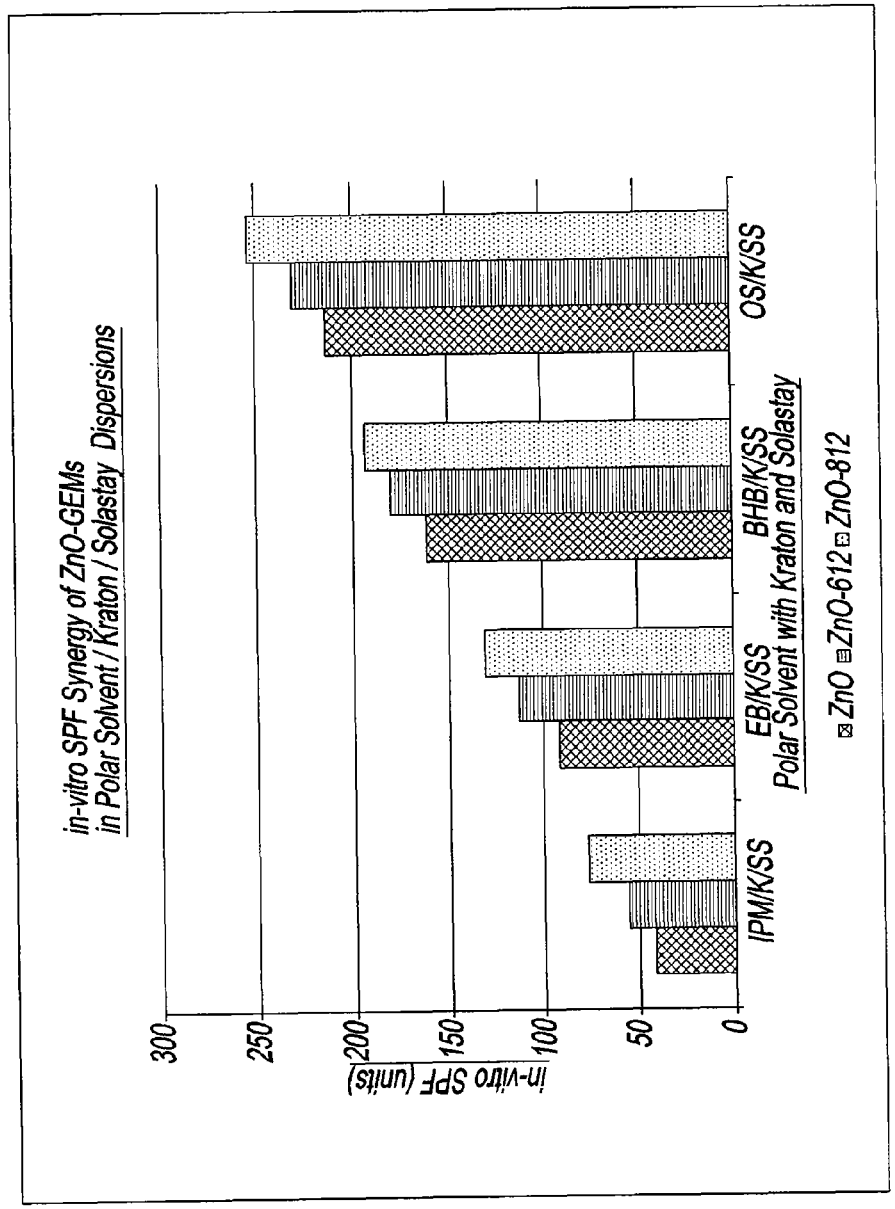

The synergies between the Kraton/Solastay combination with the ZnO and ZnO-GEMs in carrier oil dispersions are shown in FIG. 7.

The UVA1 data summarized in Table IX-B shows higher values for wavelengths at 0.5 absorbance compared to those in Table VIII-B. However, the trend was the same as noted previously in that the wavelength numbers @ 0.5 abs were similar between the plain ZnO and the ZnO-GEMs. It was in FIG. 8 that the synergistic differences in UVA1 magnitudes between the wavelengths of 340-380 nm were demonstrated amongst the dispersions.

TABLE IX-B

ZnO and ZnO-GEMs in Kraton/Solastay Carrier Oil Dispersions
Absorption Response of UVA1

| | | UVA1 ($\lambda$ nm @0.5 abs) | | | |
|---|---|---|---|---|---|
| Sample | Ratio | IPM/K | EB/K | BHB/K | OS/K |
| Solvent | Neat | — | — | — | — |
| +SS | 4.5/0.5 | 377.0 | 383.0 | 377.0 | 379.5 |
| +J208-612/SS | 4.4/0.1/0.5 | 377.0 | 384.0 | 380.0 | 380.5 |
| +J208-812/SS | 4.4/0.1/0.5 | 377.0 | 383.5 | 380.0 | 381.0 |

TABLE IX-B-continued

ZnO and ZnO-GEMs in Kraton/Solastay Carrier Oil Dispersions
Absorption Response of UVA1

| | | UVA1 ($\lambda$ nm @0.5 abs) | | | |
|---|---|---|---|---|---|
| Sample | Ratio | IPM/K | EB/K | BHB/K | OS/K |
| +ZnO/SS | 3.5/1.0/0.5 | 390.5 | 395.5 | 391.0 | 394.0 |
| +ZnO-612/SS | 3.5/1.0/0.5 | 392.0 | 398.0 | 392.0 | 395.5 |
| +ZnO-812/SS | 3.8/1.0/0.2 | — | — | — | 384.0 |
| +ZnO-812/SS | 3.5/1.0/0.5 | 392.0 | 396.0 | 392.5 | 395.0 |
| +ZnO-812/SS | 3.0/1.0/1.0 | — | — | — | 400.0 |

Dose: 0.55 mg/cm$^2$ PMMA substrate

Study 9

Samples prepared for Study 9, 10, and 11 contain carrier oils at 20% of the concentration used in Study 5, 6, 7, and 8. Therefore, the in-vitro SPF absorption response data for Study 9, 10 and 11 are approximately 20-30% of the values observed for the latter studies. The remaining amount of carrier oil was replaced with the transparent UV absorbing material, Cosmosurf CE100, to investigate its effects on the UVR absorption responses of plain ZnO and ZnO-GEMs. The dilution effect was necessary to be able to spread enough dispersion over the PMMA substrate and have measureable values that would fall below the maximum absorbance range limit of the instrument.

The data in Table X-A shows an unexpected increase in in-vitro SPF values across the aromatic and non-aromatic polar diluents, and from plain ZnO to ZnO-GEMs. Surprisingly, the in-vitro SPF data in Table X-A multiplied by a factor of 3 or 4 (OS content is ¼ amount previously used), yielded significantly larger values than those listed in Table V-A. As a conservative theoretical example, the CE100/OS/ZnO-812 (ratio of 3:1:1) SPF value of 93×3=279 SPF units is significantly higher compared to the in-vitro SPF 94 of OS/ZnO-812 (ratio 4:1) dispersion.

TABLE X-A

ZnO and ZnO-GEMs in CE100 Carrier Oil Dispersions
Absorption Response of In-Vitro SPF

| Sample | Ratio | in-vitro SPF (units) | | | |
|---|---|---|---|---|---|
| | | IPM | EB | BHB | OS |
| CE100/Solvent | 4.0/1.0 | 1 ± 0 STD | 1 ± 0 STD | 4 ± 0 STD | 8 ± 0 STD |
| +J208-612 | 3.9/1.0/0.1 | 1 ± 0 STD | 1 ± 0 STD | 3 ± 0 STD | 6 ± 0 STD |
| +J208-812 | 3.9/1.0/0.1 | 1 ± 0 STD | 1 ± 0 STD | 3 ± 0 STD | 6 ± 0 STD |
| +ZnO | 3.0/1.0/1.0 | 11 ± 0 STD | 31 ± 0 STD | 51 ± 3 STD | 46 ± 1 STD |
| +ZnO-612 | 3.0/1.0/1.0 | — | — | — | 65 ± 2 STD |
| +ZnO-812 | 3.5/1.0/0.5 | — | — | — | 38 ± 1 STD |
| +ZnO-812 | 3.0/1.0/1.0 | 19 ± 1 STD | 40 ± 2 STD | 80 ± 3 STD | 93 ± 4 STD |
| +ZnO-812 | 2.0/1.0/2.0 | — | — | — | 121 ± 3 STD |

Dose: 0.55 mg/cm$^2$ PMMA substrate

Figure 9:
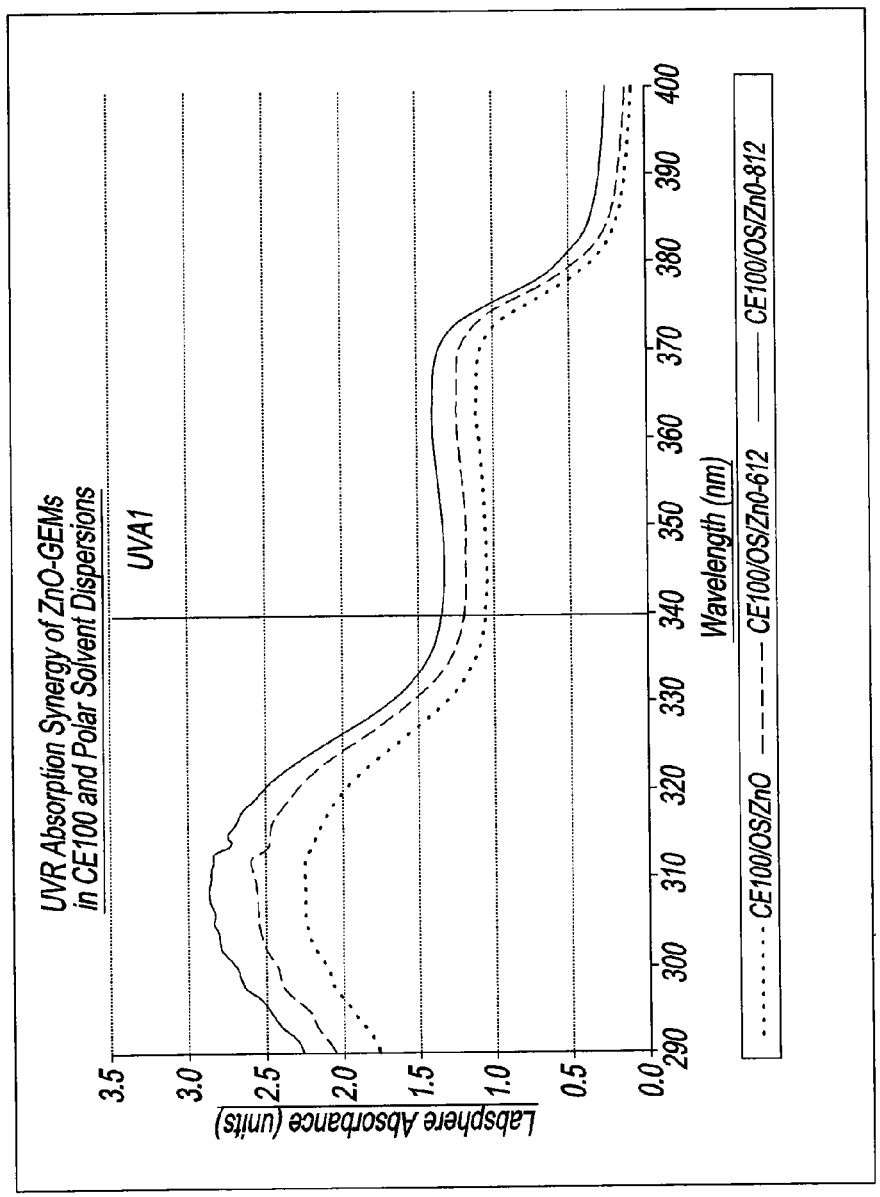

FIG. 9 illustrates the synergistic increase in UVR absorption response between plain ZnO and the ZnO-GEMS in the presence of CE100 and carrier oil. Since the GEM materials of J208-612 and J208-812 are transparent to UVR, it is unexpected that electrostatic complexation with ZnO would enhance absorption throughout the entire UVR region.

Small increases in UVA1 wavelength at 0.5 absorbance units were also noted between the ZnO and ZnO-GEM materials, as shown in Table X-B. However, FIG. 9 also clearly shows the UVA1 absorption synergy in the 340 to 400 nm region between ZnO and the ZnO-GEMs.

TABLE X-B

ZnO and ZnO-GEMs in CE100 Carrier Oil Dispersions
Absorption Response of UVA1

| Sample | Ratio | UVA1 (λ nm @0.5 abs) | | | |
|---|---|---|---|---|---|
| | | IPM | EB | BHB | OS |
| CE100/Solvent | 4.0/1.0 | — | — | — | — |
| +612 | 3.9/1.0/0.1 | — | — | — | — |
| +812 | 3.9/1.0/0.1 | — | — | — | — |
| +ZnO | 3.0/1.0/1.0 | 380.0 | 383.0 | 381.0 | 378.0 |
| +ZnO-612 | 3.0/1.0/1.0 | — | — | — | 379.0 |
| +ZnO-812 | 3.5/1.0/0.5 | — | — | — | 376.0 |
| +ZnO-812 | 3.0/1.0/1.0 | 381.0 | 384.5 | 382.0 | 381.5 |
| +ZnO-812 | 2.0/1.0/2.0 | — | — | — | 386.0 |

Dose: 0.55 mg/cm$^2$ PMMA substrate

Study 10

Figure 10:
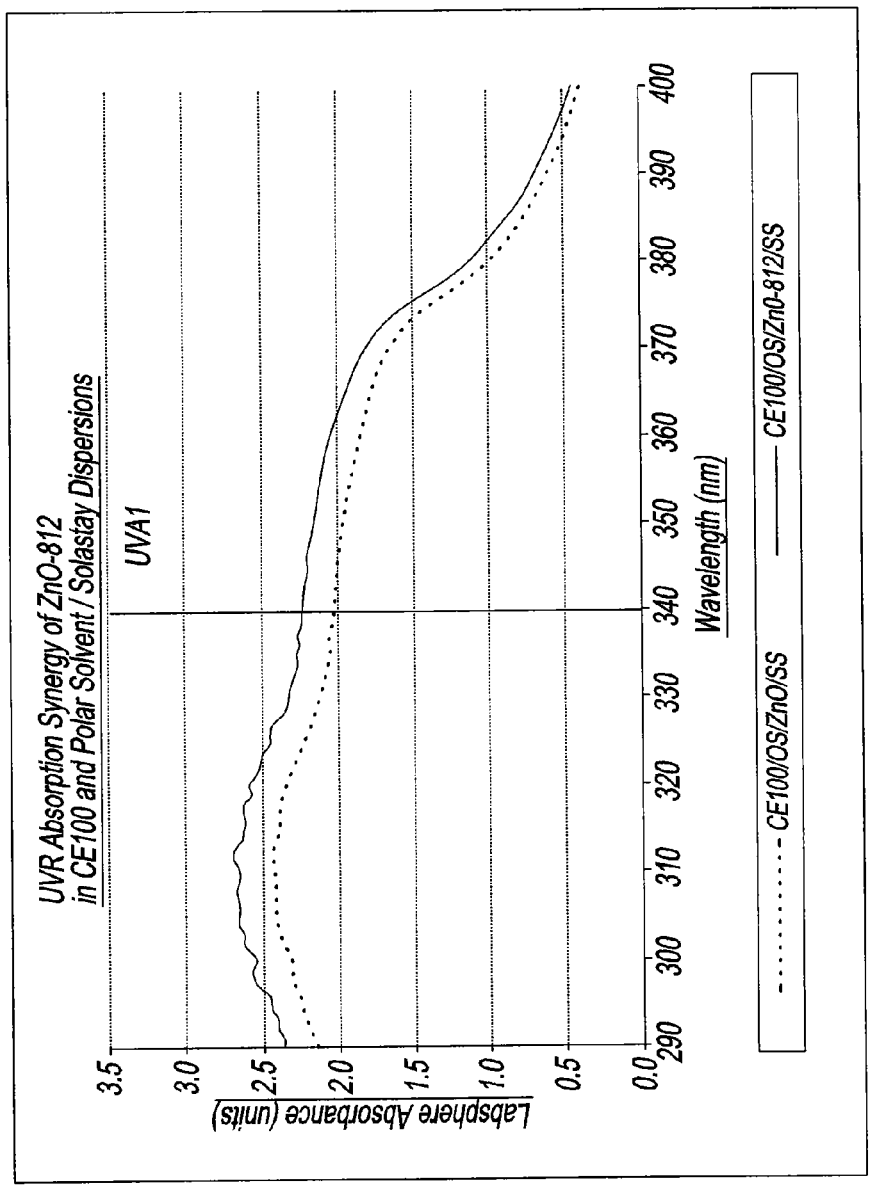

As a follow-up to Study 9, Solastay was introduced to the ZnO and ZnO-GEM CE100/carrier oil dispersions. The results were quite surprising because the in-vitro SPF values for the ZnO and ZnO-GEM CE100/Solvent/SS dispersions were higher than those for the analogous Solvent/SS dispersions. For example, CE100/Octisalate/Solastay/ZnO-812 (ratio 2.5/1.0/0.5/1.0) in-vitro SPF was 193 units, whereas the in-vitro SPF for Octisalate/Solastay/ZnO-812 (ratio 3.5/0.5/1.0) was 167 units. The difference between 193 in-vitro SPF units versus 167 in-vitro SPF units was very surprising because the former contained only about 30% of the amount of octisalate versus the latter. FIG. 10 demonstrates the further synergistic increase in UVR absorption response between plain ZnO and the ZnO-GEMS when Solastay is added to CE100 and carrier oil.

TABLE XI-A

ZnO and ZnO-GEMs in Solastay CE100 Carrier Oil Dispersions
Absorption Response of In-Vitro SPF

| Sample | Ratio | in-vitro SPF (units) | | | |
|---|---|---|---|---|---|
| | | IPM | EB | BHB | OS |
| CE100/Solvent | 4.0/1.0 | 1 ± 0 STD | 1 ± 0 STD | 4 ± 0 STD | 8 ± 0 STD |
| CE100/Solvent/SS | 3.5/1.0/0.5 | 21 ± 1 STD | 34 ± 2 STD | 55 ± 1 STD | 70 ± 3 STD |
| +ZnO | 2.5/1.0/0.5/1.0 | 56 ± 1 STD | 83 ± 2 STD | 119 ± 2 STD | 131 ± 3 STD |
| +ZnO-612 | 2.5/1.0/0.5/1.0 | — | — | — | 170 ± 2 STD |
| +ZnO-812 | 2.5/1.0/0.5/1.0 | 74 ± 2 STD | 116 ± 3 STD | 171 ± 3 STD | 193 ± 7 STD |

Dose: 0.55 mg/cm$^2$ PMMA substrate
Control Sample: CE100/SS, Ratio 4.5/0.5, in-vitro SPF = 21 ± 1 STD, UVA1 (λ nm @0.5 abs) = 381

Figure 12:
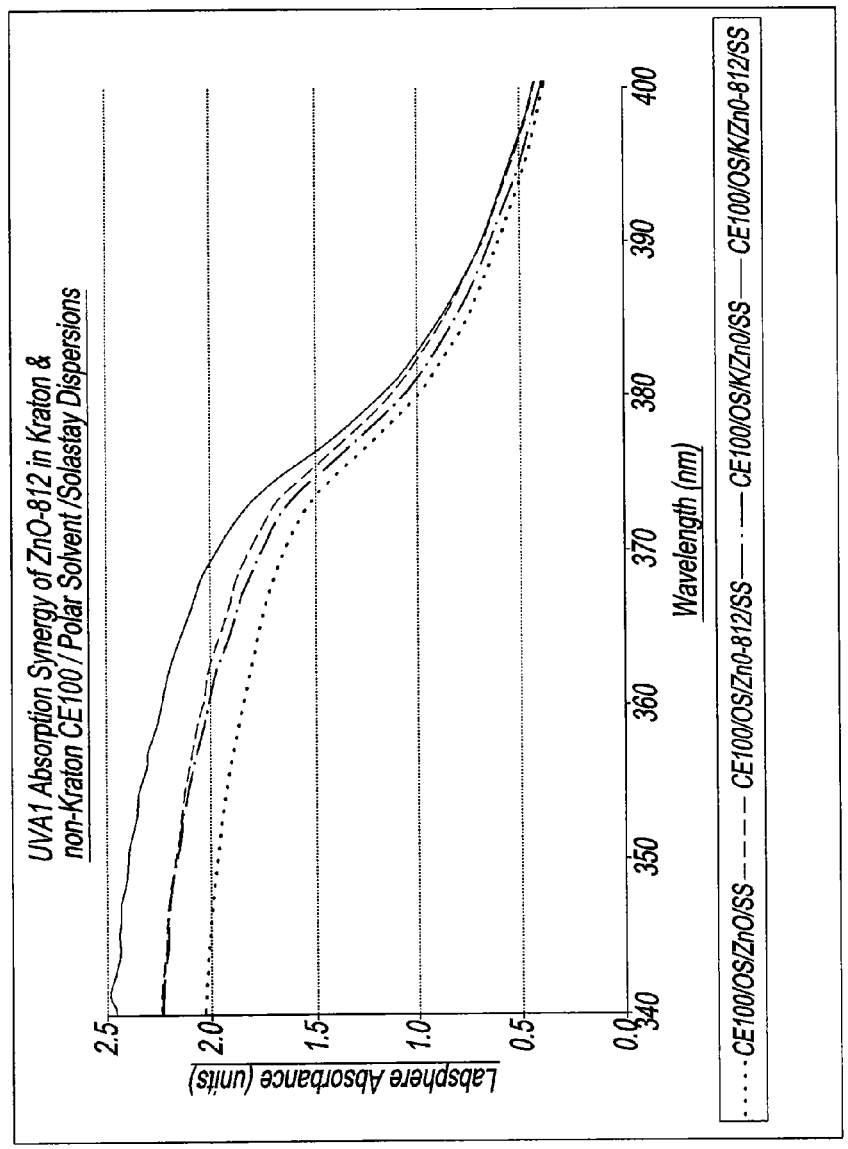

The UVA1 data presented in Table XI-B shows an overall increase in breadth of absorption, especially noted for the ZnO-812 complex. FIG. 12 clearly shows the further enhanced UVA1 absorption synergy of ZnO-812 in the 340 to 380 nm region when Solastay is present in the CE100/Solvent dispersion.

TABLE XI-B

ZnO and ZnO-GEMs in Solastay CE100 Carrier Oil Dispersions
Absorption Response of UVA1

| | | UVA1 (λ nm @0.5 abs) | | | |
|---|---|---|---|---|---|
| Sample | Ratio | IPM | EB | BHB | OS |
| CE100/Solvent | 4.0/1.0 | — | — | — | — |
| CE100/Solvent/SS | 3.5/1.0/0.5 | 380.0 | 383.0 | 381.0 | 382.0 |
| +ZnO | 2.5/1.0/0.5/1.0 | 392.5 | 395.5 | 393.0 | 394.0 |
| +ZnO-612 | 2.5/1.0/0.5/1.0 | — | — | — | 389.0 |
| +ZnO-812 | 2.5/1.0/0.5/1.0 | 392.5 | 395.0 | 394.0 | 397.0 |

Dose: 0.55 mg/cm² PMMA substrate
Control Sample: CE100/SS, Ratio 4.5/0.5, in-vitro SPF = 21 ± 1 STD, UVA1 (λ nm @0.5 abs) = 381

Study 11

Figure 11:
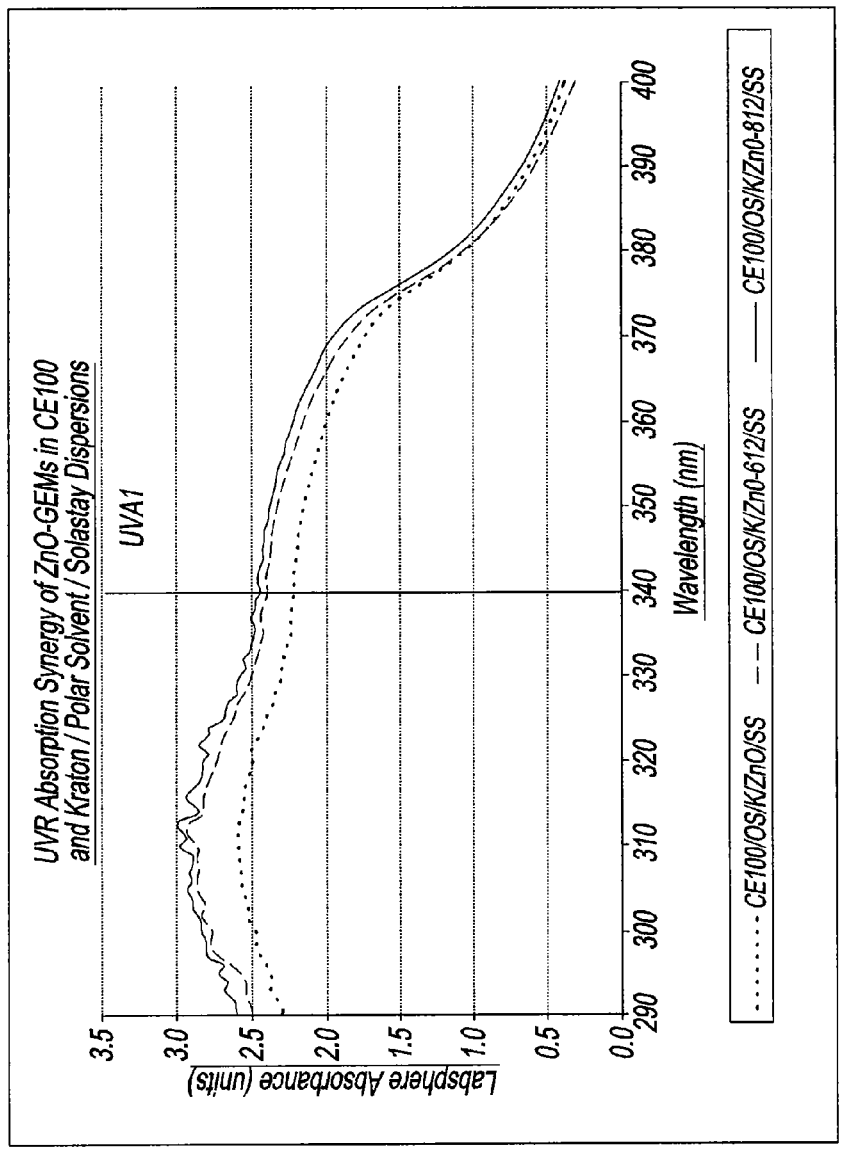

In Study 11, the effects of Kraton on UVR absorption in ZnO and ZnO-GEM dispersions containing CE100 with Solastay and carrier oil were investigated. Kraton remained uniformly dispersed in the aromatic carrier oil dispersions that contained Solastay as well as CE100. If Solastay was absent the Kraton polymer agglomerated in a non-uniform manner. The observed in-vitro SPF values were significantly higher than those values in the previous study. The combination of Kraton and Solastay synergistically enhanced the UVR absorption responses of ZnO and ZnO-GEMs in CE100/carrier oil dispersions containing BHB and octisalate. FIG. 11 demonstrates the further synergistic increase in UVR absorption response between plain ZnO and the ZnO-GEMS when Kraton is added to CE100/Carrier Oil/Solastay dispersion.

TABLE XII-A

ZnO and ZnO-GEMs in Kraton/Solastay CE100 Carrier Oil Dispersions
Absorption Response of In-Vitro SPF

| | | in-vitro SPF (units) | | | |
|---|---|---|---|---|---|
| Sample | Ratio | IPM/K | EB/K | BHB/K | OS/K |
| CE100/Solvent | 4.0/1.0 | Incompatible | Incompatible | — | — |
| CE100/Solvent/SS | 3.5/1.0/0.5 | Incompatible | Incompatible | 70 ± 3 STD | 94 ± 3 STD |
| +ZnO | 2.5/1.0/0.5/1.0 | — | — | 139 ± 4 STD | 168 ± 3 STD |
| +ZnO-612 | 2.5/1.0/0.5/1.0 | — | — | — | 213 ± 2 STD |
| +ZnO-812 | 2.5/1.0/0.5/1.0 | Incompatible | Incompatible | 201 ± 5 STD | 253 ± 4 STD |

Dose: 0.55 mg/cm² PMMA substrate

FIG. 12 clearly shows the further enhanced UVA1 absorption synergy of ZnO-812 in the 340 to 380 nm region when Kraton is added to CE100/Carrier Oil/Solastay dispersion.

TABLE XII-B

ZnO and ZnO-GEMs in Kraton/Solastay CE100 Carrier Oil Dispersions
Absorption Response of UVA1

| | | UVA1 (λ nm @0.5 abs) | | | |
|---|---|---|---|---|---|
| Sample | Ratio | IPM/K | EB/K | BHB/K | OS/K |
| CE100/Solvent | 4.0/1.0 | Incompatible | Incompatible | Incompatible | Incompatible |
| CE100/Solvent/SS | 3.5/1.0/0.5 | Incompatible | Incompatible | 381.0 | 383.0 |
| +ZnO | 2.5/1.0/0.5/1.0 | — | — | 395.0 | 395.0 |
| +ZnO-612 | 2.5/1.0/0.5/1.0 | — | — | — | 393.5 |
| +ZnO-812 | 2.5/1.0/0.5/1.0 | Incompatible | Incompatible | 395.0 | 397.0 |

Dose: 0.55 mg/cm² PMMA substrate

Study 12

A series of oil-in-water sunscreen emulsions were prepared to examine the synergistic SPF boosting effect of Kraton 1650G, Solastay and Cosmosurf CE-100 on various physical sunscreens—uncoated ZnO, and ZnO-GEM complexes. It should be noted that organic sunscreens were also included in the formulas. The in-vitro and in-vivo data are summarized separately in Table XIII below. The addition of CE-100 further boosts the efficiency of ZnO and ZO-812 to absorb UV radiation.

TABLE XIII

Oil-in-Water Emulsion Lotion SPF 30

| % | E0057-37 | E0057-13 | E0057-35 | E0057-36 | E0057-34 | E0057-10 |
|---|---|---|---|---|---|---|
| 3.00 | ZnO-812 | ZnO-812 | ZnO-812 | ZnO-812 | ZnO-812 | ZnO-812 |
| 3.00 | CE-100 | — | CE-100 | CE-100 | CE-100 | — |
| 0.26 | Kraton | Kraton | — | Kraton | — | — |
| 1.00 | Solastay | Solastay | Solastay | — | — | — |
| ... | | | | | | |
| SPF in-vitro | 75 ± 2 | 70 ± 1 | 66 ± 2 | 30 ± 1 | 29 ± 1 | 28 ± 2 |
| SPF in-vivo | 48 ± 0 | 40 ± 3 | 37 ± 2 | 39 ± 2 | 38 ± 0 | 32 ± 0 |

| % | E0057-29 | E0057-09 | E0057-35 | E0057-36 | E0057-34 | E0057-06 |
|---|---|---|---|---|---|---|
| 3.00 | ZnO | ZnO | ZnO | ZnO | ZnO | ZnO |
| 3.00 | CE-100 | — | CE-100 | CE-100 | CE-100 | — |
| 0.26 | Kraton | Kraton | — | Kraton | — | — |
| 1.00 | Solastay | Solastay | Solastay | — | — | — |
| ... | | | | | | |
| SPF in-vitro | 68 ± 2 | 60 ± 2 | 57 ± 1 | 29 ± 1 | 27 ± 0 | 26 ± 1 |
| SPF in-vivo | 41 ± 0 | 41 ± 3 | Not tested | Not tested | 31 ± 0 | 32 ± 1 |

First, it should be noted that the trends noted in the in-vitro SPF data of Table XIII match the trends noted in the oil phases summarized in Tables I-A through XII-A.

Surprisingly, for a low (3%) concentration level of physical sunscreen, there was an increase of 16 in-vivo SPF units for ZnO-812 with no adjuvants compared to the formula with the synergistic system (Kraton, Solastay, CE-100) of adjuvants. Interestingly, in the analogous ZnO series, there was an increase of 9 in-vivo SPF units for ZnO with no adjuvants compared to the formula with the synergistic system (Kraton, Solastay, CE-100) of adjuvants. At higher concentrations of ZnO and ZnO-812 it is possible that more of a differential would be noted in the in-vivo SPF data.

Ingredient ranges were varied as follows:

| | |
|---|---|
| ZnO | 0.00, 3.00 |
| ZnO-812 | 0.00, 3.00 |
| Cosmosurf CE-100 | 0.00, 3.00% |
| Kraton 1650G | 0.00, 0.26% |
| Solastay | 0.00, 1.00% |
| Octisalate | 0.00, 5.00% |
| Homosalate | 0.00, 10.00% |
| Octocrylene | 0.00, 2.40% |

Study 13

A series of water-in-oil sunscreen lotion emulsions were prepared to confirm that the synergistic in-vitro effects noted above would translate to an inverse emulsion. Also, ingredient ranges were varied as follows:

| | |
|---|---|
| ZnO | 0.00, 3.00-15.00% |
| ZnO-812 | 0.00, 3.00-15.00% |
| Cosmosurf CE-100 | 0.00, 0.50-20.00% |
| Kraton 1650G | 0.00, 0.10-0.52% |
| Solastay | 0.00, 1.00-3.00% |
| Octisalate | 0.00, 3.00-5.00% |
| Homosalate | 0.00, 6.00-10.00% |
| Octocrylene | 0.00, 2.40-5.00% |
| Avobenzone | 0.00, 2.00-3.00% |

The in-vitro data summarized in Table IV below confirm that the combination of Kraton and Solastay synergistically enhances the UV absorption ability of ZnO and ZnO-812. The presence of Cosmosurf CE-100 further enhances that synergy as indicated in Table XIV below. This holds true despite the fact that, as previously established (e.g., in Table IIA above, sample ID #0008-85-1), CE100 has minimal if any SPF on its own.

TABLE XIV

Water-in-Oil Emulsion Lotion SPF 30

| % | E0057-141 | E0057-135 | % | E0091-015 | E0091-011 |
|---|---|---|---|---|---|
| 3.00 | ZnO-812 | ZnO-812 | 5.00 | ZnO-812 | ZnO-812 |
| 3.00 | CE-100 | — | 3.00 | CE-100 | — |
| 0.26 | Kraton | Kraton | 0.26 | Kraton | Kraton |
| 1.00 | Solastay | Solastay | 1.00 | Solastay | Solastay |
| ... | | | ... | | |
| SPF in-vitro | 227 ± 4 | 212 ± 3 | SPF in-vitro | 232 ± 2 | 217 ± 3 |

| % | E0057-138 | E0057-09 | % | E0091-012 | E0091-010 |
|---|---|---|---|---|---|
| 3.00 | ZnO | ZnO | 5.00 | ZnO | ZnO |
| 3.00 | CE-100 | — | 3.00 | CE-100 | — |
| 0.26 | Kraton | Kraton | 0.26 | Kraton | Kraton |
| 1.00 | Solastay | Solastay | 1.00 | Solastay | Solastay |
| ... | | | ... | | |
| SPF in-vitro | 211 ± 6 | 191 ± 2 | SPF in-vitro | 218 ± 1 | 203 ± 3 |

Study 14

A series of oil-in-water sunscreen crème emulsions were prepared to confirm that the synergistic in-vitro effects noted above would translate to a different product form, in this case a cream (Table XV) and a stick (Table XVI). Ingredient ranges were varied as follows:

| | |
|---|---|
| ZnO | 0.00, 3.00-15.00% |
| ZnO-812 | 0.00, 3.00-15.00% |
| Cosmosurf CE-100 | 0.00, 0.50-20.00% |
| Kraton 1650G | 0.00, 0.10-0.52% |
| Solastay | 0.00, 1.00-3.00% |
| Octisalate | 0.00, 3.00-5.00% |
| Homosalate | 0.00, 6.00-10.00% |
| Octocrylene | 0.00, 2.40-5.00% |
| Avobenzone | 0.00, 2.00-3.00% |

The in-vitro data summarized in Table XV confirm that the combination of Kraton and Solastay synergistically enhances the UV absorption ability of ZnO and ZnO-812 in cream form. The presence of Cosmosurf CE-100 further enhances that synergy as indicated.

TABLE XV

Oil-in-Water Emulsion Crème SPF 30

| % | E0057-083 | E0057-079 | % | E0057-124 | E0057-120 |
|---|---|---|---|---|---|
| 3.00 | ZnO-812 | ZnO-812 | 5.00 | ZnO-812 | ZnO-812 |
| 3.00 | CE-100 | — | 3.00 | CE-100 | — |
| 0.26 | Kraton | Kraton | 0.26 | Kraton | Kraton |
| 1.00 | Solastay | Solastay | 1.00 | Solastay | Solastay |
| ... | | | ... | | |
| SPF in-vitro | 165 ± 2 | 135 ± 2 | SPF in-vitro | 128 ± 1 | 117 ± 1 |

| % | E0057-081 | E0057-078 | % | E0057-121 | E0057-119 |
|---|---|---|---|---|---|
| 3.00 | ZnO | ZnO | 5.00 | ZnO | ZnO |
| 3.00 | CE-100 | — | 3.00 | CE-100 | — |
| 0.26 | Kraton | Kraton | 0.26 | Kraton | Kraton |
| 1.00 | Solastay | Solastay | 1.00 | Solastay | Solastay |
| ... | | | ... | | |
| SPF in-vitro | 150 ± 3 | 124 ± 3 | SPF in-vitro | 116 ± 0 | 109 ± 3 |

A series of sunscreen sticks were prepared to confirm that the synergistic in-vitro effects noted above would translate to a different product form. Ingredient ranges were varied as follows:

| | |
|---|---|
| ZnO | 0.00, 3.00-15.00% |
| ZnO-812 | 0.00, 3.00-15.00% |
| Cosmosurf CE-100 | 0.00, 0.50-20.00% |
| Kraton 1650G | 0.00, 0.10-0.52% |
| Solastay | 0.00, 1.00-3.00% |
| Octisalate | 0.00, 3.00-5.00% |
| Homosalate | 0.00, 6.00-10.00% |
| Octocrylene | 0.00, 2.40-5.00% |
| Avobenzone | 0.00, 2.00-3.00% |

The in-vitro data summarized in Table XVI confirm that the combination of Kraton and Solastay synergistically enhances the UV absorption ability of ZnO and ZnO-812 in a stick form. The presence of Cosmosurf CE-100 further enhances that synergy as indicated in the Table below.

TABLE XVI

Sunscreen Stick SPF 30

| % | E0057-103 | E0057-097 | E0057-101 |
|---|---|---|---|
| 3.00 | ZnO-812 | ZnO-812 | ZnO-812 |
| 3.00 | CE-100 | — | CE-100 |
| 0.26 | Kraton | Kraton | — |
| 1.00 | Solastay | Solastay | — |
| ... | | | |
| SPF in-vitro | 91 ± 0 | 84 ± 3 | 64 ± 3 |

TABLE XVI-continued

Sunscreen Stick SPF 30

| % | E0057-100 | E0057-078 | E0057-098 |
|---|---|---|---|
| 3.00 | ZnO | ZnO | ZnO |
| 3.00 | CE-100 | — | CE-100 |
| 0.26 | Kraton | Kraton | — |
| 1.00 | Solastay | Solastay | — |
| ... | | | |
| SPF in-vitro | 81 ± 1 | 67 ± 4 | 56 ± 1 |

Study 15

Previously, the SPF boosting effects of Kraton 1650G and Solastay on uncoated ZnO and GEM (gelling electrostatic matrix) ZnO were illustrated. In Table XVII, ZnO is complexed with Triethoxycaprylylsiloxane (TECS). The data indicate that the combination of Kraton 1650G and Solastay boosted the UV absorption ability of the ZnO-TECS, and that the addition of CE-100 further boosted that capability as shown below.

TABLE XVII

ZnO Coated with Triethoxycaprylylsiloxane (TECS) and Kratons

| | E0091-095-1 ZnO-TECS | E0057-078 ZnO-TECS | E0057-098 ZnO-TECS |
|---|---|---|---|
| | CE-100 | — | — |
| | Kraton 1650G | Kraton 1650G | Kraton 1650G |
| | Solastay | Solastay | — |
| SPF in-vitro | 107 ± 3 | 99 ± 1 | 26 ± 1 |
| | E3088-75-8 | E0057-075-10 | E0057-075-10 |
| For Relative Comparison | ZnO-812 CE-100 Kraton 1650G Solastay | ZnO-812 — Kraton 1650G Solastay | ZnO-812 — Kraton 1650G Solastay |
| SPF in-vitro | 156 ± 10 | 129 ± 4 | 52 ± 3 |

Study 16

In another study, the SPF boosting effects of Kraton 1650G and Solastay on two complexed titanium dioxides was examined. The data indicated that the combination of Kraton 1650G and Solastay boosted the UV absorption ability of the $TiO_2$-M262 and $TiO_2$-JTTO, and that the addition of CE-100 further boosted that capability as shown below.

TABLE XVIII

TiO$_2$ Complexed with Alumina/Dimethicone (M262) or Alumina/Methicone (JTTO)

|  | E0091-078-10 TiO$_2$-M262 | E0091-077-4 TiO$_2$-M262 | E0091-077-3 TiO$_2$-M262 |
|---|---|---|---|
|  | CE-100 Kraton 1650G Solastay | — Kraton 1650G Solastay | — Kraton 1650G — |
| SPF in-vitro | 130 ± 2 | 103 ± 5 | 48 ± 2 |

|  | E0091-078-13 TiO$_2$-JTTO | E0091-077-7 TiO$_2$-JTTO | E0091-077-4 TiO$_2$-JTTO |
|---|---|---|---|
|  | CE-100 Kraton 1650G Solastay | — Kraton 1650G Solastay | — Kraton 1650G — |
| SPF in-vitro | 144 ± 2 | 120 ± 3 | 103 ± 5 |

Finally, in the data of Tables II-XVIII, Kraton G1650 was used. However, as previously discussed, other Kraton® polymers are suitable, such as Kraton D1164PT (styrene/isoprene copolymer) and Kraton G1702HU (hydrogenated styrene/isoprene copolymer). In testing data similar to that provided above, these two additional Kratons were evaluated based on their effectiveness in boosting SPF of ZnO and ZnO-812. Kraton 1650G was found to be the most effective, but the other Kraton polymers may be preferred in other compositions or for other reasons. It is also expected that the trends noted for the octisalate solvent/Kraton variants would be the same for the less polar solvents of Hallbrite BHB, Finsolv EB, and isopropyl myristate.

While the present disclosure has been described with reference to one or more exemplary embodiments, it will be understood by those skilled in the art that various changes may be made and equivalents may be substituted for elements thereof without departing from the scope of the present disclosure. In addition, many modifications may be made to adapt a particular situation or material to the teachings of the disclosure without departing from the scope thereof. Therefore, it is intended that the present disclosure not be limited to the particular embodiment(s) disclosed as the best mode contemplated.

What is claimed is:

1. A synergistic combination comprising:
a physical sunscreen present in a amount of 0.5% w/w to 30% w/w;
ethylhexyl methoxycrylene present in an amount of 0.1% w/w to 6.0% w/w, wherein said ethylhexyl methoxycrylene is present in an amount that is 0.2 to 5.0 times the amount of said physical sunscreen;
a compound having multiple phenyl groups present in an amount of 0.1% w/w to 4.0% w/w and is 0.05 to 2.2 times the amount of said physical sunscreen, wherein said compound having multiple phenyl groups is selected from the group consisting of benzene sulfonic acids, salts of benzene sulfonic acids, styrene/ethylene/butylene block copolymer, and any combinations thereof;
a carrier oil present in an amount that is 0.95 to 41.8 times the amount of said physical sunscreen; and
optionally, at least one of a silicone surfactant and a dispersant.

2. A synergistic combination comprising:
a physical sunscreen present in an amount of 0.5% w/w to 30% w/w;
ethylhexyl methoxycrylene present in an amount of 0.1% w/w to 6.0% w/w, wherein said ethylhexyl methoxycrylene is present in an amount that is 0.2% to 5.0 times the amount of said physical sunscreen;
a compound having multiple phenyl groups comprising a styrene/ethylene/butylene block copolymer present in an amount of 0.1% w/w to 4.0% w/w and is 0.05 to 2.2 times the amount of said physical sunscreen;
a carrier oil present in an amount that is 0.95 to 41.8 times the amount of said physical sunscreen; and
optionally, at least one of a silicone surfactant and a dispersant.

3. A synergistic combination comprising:
a physical sunscreen present in an amount of 0.5% w/w to 30% w/w;
ethylhexyl methoxycrylene present in an amount of 0.1% w/w to 6.0% w/w, wherein said ethylhexyl methoxycrylene is present in an amount that is 0.2 to 5.0 times the amount of said physical sunscreen;
a compound having multiple phenyl groups selected from the group consisting of benzene sulfonic acid, salts of benzene sulfonic adds, styrenic block copolymers with a hydrogenated midblock of styrene-ethylene/butylene-styrene, styrenic block copolymers with a hydrogenated midblock of styrene-ethylene/propylene-styrene, styrene/butadiene/styrene block copolymers, styrene/isoprene/styrene block copolymers, ethylene/butadiene/styrene block copolymer, ethylene/propylene/styrene block copolymer, styrene/ethylene/butylene block copolymer, styrene/propylene/butadiene block copolymer, derivatives of any of said compounds having multiple phenyl groups, and any combinations thereof, wherein the compound having multiple phenyl groups is present in an amount of 0.2% w/w to 1.0% w/w and is 0.05 to 2.2 times the amount of said physical sunscreen;
a carrier oil present in an amount that is 0.95 to 41.8 times the amount of said physical sunscreen; and
optionally, at least one of a silicone surfactant and a dispersant.

4. A synergistic combination comprising:
a physical sunscreen present in an amount of 0.5% w/w to 30% w/w;
ethylhexyl methoxycrylene present in an amount of 0.2% w/w to 2.0% w/w, wherein said ethylhexyl methoxycrylene is present in an amount that is 0.2 to 5.0 times the amount of said physical sunscreen;
a compound having multiple phenyl groups selected from the group consisting of benzene sulfonic acids, salts of benzene sulfonic adds, styrenic block copolymers with a hydrogenated midblock of styrene-ethylene/butylene-styrene, styrenic block copolymers with a hydrogenated midblock of styrene-ethylene/propylene-styrene, styrene/butadiene/styrene block copolymers, styrene/isoprene/styrene block copolymers, ethylene/butadiene/styrene block copolymer, ethylene/propylene/styrene block copolymer, styrene/ethylene/butylene block copolymer, styrene/propylene/butadiene block copolymer, derivatives of any of said compounds having multiple phenyl groups, and any combination thereof, wherein said compound having multiple phenyl groups is present in an amount of 0.1% w/w to 4.0% w/w and is 0.05 to 2.2 times the amount of said physical sunscreen;
a carrier oil, wherein the carrier oil is present in an amount that is 0.95 to 41.8 times the amount of physical sunscreen; and
optionally, at least one of a silicone surfactant and a dispersant.

5. A synergistic combination comprising:
a physical sunscreen in an amount of 0.5% w/w to 30% w/w;
ethylhexyl methoxycrylene present in an amount of 0.1% w/w to 6.0% w/w, wherein the ethylhexyl methoxycrylene is present in an amount that is 0.2 to 5.0 times the amount of the physical sunscreen;
a compound having multiple phenyl groups selected from the group consisting of benzene sulfonic acids, salts of benzene sulfonic adds, styrenic block copolymers with a hydrogenated midblock of styrene-ethylene/butylene-styrene, styrenic block copolymers with a hydrogenated midblock of styrene-ethylene[propylene-styrene, styrene/butadiene/styrene block copolymers, styrene/isoprene block copolymers, ethylene/butadiene/styrene block copolymer, ethylene/propylene/styrene block copolymer, styrene/ethylene/butylene block copolymer, styrene/propylene/butadiene block copolymer, derivatives of any of said compounds having multiple phenyl groups, and any combinations thereof, wherein said compounds having multiple phenyl groups is present in an amount of 0.1% w/w to 4.0% w/w and is 0.05 to 2.2 times the amount of the physical sunscreen;
carrier oil, wherein the carrier oil is an amount in an amount that is 0.95 to 41.8 times the amount of the physical sunscreen; and
optionally, at least one of a silicone surfactant and a dispersant,
wherein said dispersant is octyldodecyl-propyl-citrate present in an amount of 0.5% w/w to 20% w/w.

6. A synergistic combination comprising
a physical sunscreen present in an amount of 0.5% w/w to 30% w/w;
ethylhexyl methoxycrylene present in an amount of 0.1% w/w to 6.0% w/w, wherein said ethylhexyl methoxycrylene is present in an amount that is 0.2 to 5.0 times the amount of said physical sunscreen;
a compound having multiple phenyl groups selected from the group consisting of benzene sulfonic acids, salts of benzene sulfonic adds, styrenic block copolymers with a hydrogenated midblock of styrene-ethylene/butylene-styrene, styrenic block copolymers with a hydrogenated midblock of styrene-ethylene[propylene-styrene, styrene/butadiene/styrene block copolymers, styrene/isoprene/styrene block copolymers, ethylene/butadiene/styrene block copolymer, ethylene/propylene/styrene block copolymer, styrene/ethylene/butylene block copolymer, styrene/propylene/butadiene block copolymer, derivatives of any said compounds having multiple phenyl groups, and any combinations thereof, wherein said compound having multiple phenyl groups is present in am amount of 0.1% w/w to 4.0% w/w and is 0.05 to 2.2 times the amount of said physical sunscreen;
a carrier oil present in an amount that is 0.95 to 41.8 times the amount of said physical sunscreen; and
optionally, at least one of a silicone surfactant, wherein said silicone surfactant is present, and is selected from the group consisting of lauryl polyethylene glycol-8 dimethicone, a derivative thereof, or a combination of the two, and a dispersant.

7. A synergistic combination comprising
a physical sunscreen present in an amount of 0.5% w/w to 30% w/w;
ethylhexyl methoxycrylene present in an amount of 0.1% w/w to 6.0% w/w that is 0.2 to 5.0 times the amount of said physical sunscreen;
a compound having multiple phenyl groups selected from the group consisting of benzene sulfonic acids, salts of benzene sulfonic adds, styrenic block copolymers with a hydrogenated midblock of styrene-ethylene/butylene-styrene, styrenic block copolymers with a hydrogenated midblock of styrene-ethylene/propylene-styrene styrene/butadiene/styrene block copolymers, styrene/isoprene/styrene block copolymers, ethylene/butadiene/styrene block copolymer, ethylene/propylene/styrene block copolymer, styrene/ethylene/butylene block copolymer, styrene/propylene/butadiene block copolymer, derivatives of any said compound having multiple phenyl groups, and any combinations thereof, wherein said compound having multiple phenyl groups is present in an amount of 0.1% w/w to 4.0% w/w that is 0.05 to 2.2 times the amount of said physical sunscreen;
a carrier oil present in an amount that is 0.95 to 41.8 times the amount of said physical sunscreen; and
optionally, at least one of a silicone surfactant present in an amount of 0.1% w/w to 10.0% w/w and a dispersant.

8. A synergistic combination comprising:
a physical sunscreen present in a amount of 0.5% w/w to 30% w/w;
ethylhexyl methoxycrylene present in an amount of 0.1% w/w to 6.0% w/w that is 0.2 to 5.0 times the amount of said physical sunscreen;
a compound having multiple phenyl groups selected from the group consisting of benzene sulfonic acids, salts of benzene sulfonic adds, styrenic block copolymers with a hydrogenated midblock of styrene-ethylene/butylene-styrene, styrenic block copolymers with a hydrogenated midblock of styrene-ethylene/propylene-styrene, styrene/butadiene/styrene block copolymers, styrene/isoprene/styrene block copolymers, ethylene/butadiene/styrene block copolymers, ethylene/propylene/styrene block copolymer, styrene/ethylene/butylene block copolymer, styrene/propylene/butadiene block copolymer, derivatives of any said compounds having multiple phenyl groups, and any combinations thereof, wherein said compound having multiple phenyl groups is present in an amount of 0.1% w/w to 4.0% w/w that is 0.05 to 2.2 times the amount of said physical sunscreen;
a carrier oil selected from the group consisting of mineral oil, isopropyl myristate, butyloctyl salcyclate, and any combinations thereof, present in an amount that is 0.95 to 41.8 times the amount of said physical sunscreen; and
optionally, at least one of the silicone surfactant and a dispersant.

9. A sunscreen composition comprising a synergistic combination comprising:
a physical sunscreen present in a amount of 0.5% w/w to 30% w/w;
ethylhexyl methoxycrylene present in an amount of 0.1% w/w to 6.0% w/w that is 0.2 to 5.0 times the amount of said physical sunscreen;
a compound having multiple phenyl groups selected from the group consisting of benzene sulfonic acids, salts of benzene sulfonic adds, styrenic block copolymers with a hydrogenated midblock of styrene-ethylene/butylene-styrene, styrenic block copolymers with a hydrogenated midblock of styrene-ethylene/propylene-styrene, styrene/butadiene/styrene block copolymers, styrene/isoprene/styrene block copolymers, ethylene/butadiene/styrene block copolymer, ethylene/propylene/styrene block copolymer, styrene/ethylene/butylene block copolymer, styrene/propylene/butadiene block copolymer, derivatives of any said compound having multiple phenyl groups, and any combinations thereof, wherein said compound having multiple phenyl groups is present in an amount of 0.1% w/w to 4.0% w/w that is 0.05 to 2.2 times the amount of said physical sunscreen;

a carrier oil present in an amount that is 0.95 to 41.8 times the amount of said physical sunscreen; and optionally, at least one of the silicone surfactant and a dispersant; and water, wherein said sunscreen composition is an oil-in-water emulsion.

10. A sunscreen composition comprising a synergistic combination comprising:

a physical sunscreen present in an amount of 0.5% w/w to 30% w/w;

ethylhexyl methoxycrylene present in an amount of 0.1% w/w to 6.0% w/w that is 0.2 to 5.0 times the amount of said physical sunscreen;

a compound having multiple phenyl groups selected from the group consisting of benzene sulfonic acids, salts of benzene sulfonic adds, styrenic block copolymers with a hydrogenated midblock of styrene-ethylene/butylene-styrene, styrenic block copolymers with a hydrogenated midblock of styrene-ethylene/propylene-styrene, styrene/butadiene/styrene block copolymers, styrene/isoprene/styrene block copolymers, ethylene/butadiene/styrene block copolymers, ethylene/propylene/styrene block copolymer, styrene/ethylene/butylene block copolymer, styrene/propylene/butadiene block copolymer, derivatives of any said compounds having multiple phenyl groups, and any combinations thereof, wherein said compound having multiple phenyl groups is present in an amount of 0.1% w/w to 4.0% w/w that is 0.05 to 2.2 times the amount of said physical sunscreen;

a carrier oil present in an amount that is 0.95 to 41.8 times the amount of said physical sunscreen; and optionally, at least one of the silicone surfactant and a dispersant; and water, wherein said sunscreen composition is a water-in-oil emulsion.

11. A synergistic combination comprising:

a physical sunscreen present in a amount of 0.5% w/w to 30% w/w;

ethylhexyl methoxycrylene present in an amount of 0.1% w/w to 6.0% w/w, wherein said ethylhexyl methoxycrylene is present in an amount that is 0.2 to 5.0 times the amount of said physical sunscreen;

a compound having multiple phenyl groups in an amount 0.1% w/w to 4.0% w/w and is 0.05 to 2.2 times the amount of said physical sunscreen, wherein said compound having multiple phenyl groups is selected from the group consisting of benzene sulfonic acids, salts of benzene sulfonic acids, styrene/ethylene/butylene block copolymer, and any combinations thereof;

a carrier oil present in an amount that is 0.95 to 41.8 times the amount of said physical sunscreen;

an organic sunscreen; and optionally, at least one of a silicone surfactant and a dispersant.

12. A synergistic combination comprising:

a physical sunscreen present in an amount of 0.5% w/w to 30% w/w;

ethylhexyl methoxycrylene present in an amount of 0.1% w/w to 6.0% w/w, wherein said ethylhexyl methoxycrylene is present in an amount that is 0.2 to 5.0 times the amount of said physical sunscreens;

a compound having multiple phenyl groups present in an amount of 0.1% w/w to 4.0% w/w and is 0.05 to 2.2 times the amount of said physical sunscreen, wherein said compound having multiple phenyl groups is selected from the group consisting of benzene sulfonic acids, salts of benzene sulfonic acids, styrene/ethylene/butylene block copolymer, and any combinations thereof;

a carrier oil present in an amount that is 0.95 to 41.8 times the amount of said physical sunscreen;

an organic sunscreen selected from the group consisting of octisalate, homosalte, octocrylene, avobenzone, and any combinations thereof; and optionally, at least one of a silicone surfactant and a dispersant.

13. A synergistic combination comprising:

a physical sunscreen selected from the group consisting of titanium dioxide, zinc oxide, coated zinc oxide, or a combination thereof, present in an amount of 0.5% w/w to 30% w/w;

ethylhexyl methoxycrylene present in an amount of 0.2% w/w to 2.0% w/w that is 0.20 to 5.0 times the amount of said physical sunscreen;

a compound having multiple phenyl groups comprising a styrene/ethylene/butylene block copolymer present in an amount of 0.2% w/w to 1.0% w/w that is 0.5 to 2.2 times the amount of said physical sunscreen; and a carrier oil present in an amount that is 0.95 to 41.8 times the amount of said physical sunscreen.

14. A synergistic combination comprising:

a physical sunscreen from the group consisting of titanium dioxide, zinc oxide, coated zinc oxide, or a combination thereof, present in an amount of 0.5% w/w to 30% w/w;

ethylhexyl methoxycrylene present in an amount of 0.2% w/w to 2.0% w/w that is 0.20 to 5.0 times the amount of said physical sunscreen;

a compound having multiple phenyl groups selected from the group consisting of benzene sulfonic acids, salts of benzene sulfonic acids, styrene/ethylene/butylene block copolymer, and any combinations thereof, wherein said compound having multiple phenyl groups is present in an amount of 0.2% w/w to 1.0% w/w that is 0.05 to 2.2 times the amount of said physical sunscreen;

a carrier oil present in an amount that is 0.95 to 41.8 times the amount of said physical sunscreen; and octyldodecyl-propyl-citrate present in an amount of 0.5% w/w to 20% w/w.

15. A synergistic combination comprising:

a physical sunscreen selected from the group consisting of titanium dioxide, zinc oxide, coated zinc oxide, or a combination thereof, present in an amount of 0.5% w/w to 30% w/w;

ethylhexyl methoxycrylene present in an amount of 0.2% w/w to 2.0% w/w that is 0.20 to 5.0 times the amount of said physical sunscreen;

a compound having multiple phenyl groups selected from the group consisting of benzene sulfonic acids, salts of benzene sulfonic acids, styrene/ethylene/butylene block copolymer, and any combinations thereof, wherein said compound having multiple phenyl groups is present in an amount of 0.2% w/w to 1.0% w/w that is 0.05 to 2.2 times the amount of said physical sunscreen;

a carrier oil present in an amount that is 0.95 to 41.8 times the amount of said physical sunscreen; and a silicone surfactant present in an amount of 0.1% w/w to 10.0% w/w and selected from the group consisting of lauryl polyethylene glycol-8 dimethicone, a derivative thereof, or a combination of the two.

\* \* \* \* \*